United States Patent
Zhang et al.

(10) Patent No.: US 11,292,811 B2
(45) Date of Patent: Apr. 5, 2022

(54) LONG-ACTING PRODRUGS OF ENTECAVIR, PREPARING METHODS AND USES THEREOF

(71) Applicant: GUANGZHOU HENOVCOM BIOSCIENCE CO. LTD, Guangzhou (CN)

(72) Inventors: Jiancun Zhang, Guangzhou (CN); Deyao Li, Guangzhou (CN); Yiqian Zhou, Guangzhou (CN); Yiwu Wu, Guangzhou (CN); Yan Liu, Guangzhou (CN)

(73) Assignee: GUANGZHOU HENOVCOM BIOSCIENCE CO. LTD, Guangzhou (CN)

( * ) Notice: Subject to any disclaimer, the term of this patent is extended or adjusted under 35 U.S.C. 154(b) by 0 days.

(21) Appl. No.: 16/650,920

(22) PCT Filed: Sep. 29, 2018

(86) PCT No.: PCT/CN2018/108663
§ 371 (c)(1),
(2) Date: Mar. 26, 2020

(87) PCT Pub. No.: WO2019/062924
PCT Pub. Date: Apr. 4, 2019

(65) Prior Publication Data
US 2020/0239513 A1 Jul. 30, 2020

(30) Foreign Application Priority Data
Sep. 29, 2017 (CN) .......................... 201710903592.1

(51) Int. Cl.
*C07H 19/16* (2006.01)
*A61K 9/00* (2006.01)

(52) U.S. Cl.
CPC ........... *C07H 19/16* (2013.01); *A61K 9/0019* (2013.01)

(58) Field of Classification Search
None
See application file for complete search history.

(56) References Cited

FOREIGN PATENT DOCUMENTS

| | | |
|---|---|---|
| CN | 1566118 A | 1/2005 |
| CN | 1699366 A | 11/2005 |
| CN | 1907987 A | 2/2007 |
| CN | 101003536 A | 7/2007 |
| CN | 101096370 A | 1/2008 |
| CN | 101781300 A | 7/2010 |
| CN | 104292290 A | 1/2015 |
| CN | 105585569 A | 5/2016 |
| KR | 20110026311 A | 3/2011 |
| WO | 2018/066947 A1 | 4/2018 |

OTHER PUBLICATIONS

Zheng, CN 101134769, May 3, 2008, machine translation. (Year: 2008).*
CN 105585569, May 18, 2016. (Year: 2016).*
WO 2018066947 A1, Apr. 4, 2018, machine translation. (Year: 2018).*
International Search Report dated Dec. 29, 2018 for PCT/CN2018/108663.

* cited by examiner

*Primary Examiner* — Layla D Berry
(74) *Attorney, Agent, or Firm* — Schmeiser, Olsen & Watts, LLP

(57) ABSTRACT

Provided are a long-acting prodrug of Entecavir, preparation method and use thereof, wherein the prodrug of Entecavir has a structure of formula I. The prodrug of Entecavir can be released slowly, sustainably and steady, and converted to active compound of Entecavir to achieve a long-acting effect.

7 Claims, 2 Drawing Sheets

LONG-ACTING PRODRUGS OF ENTECAVIR, PREPARING METHODS AND USES THEREOF

CROSS-REFERENCE TO RELATED APPLICATIONS

This application claims priority to PCT Application No. PCT/CN2018/108663, having a filing date of Sep. 29, 2018, which is based on Chinese Application No. 201710903592.1, having a filing date of Sep. 29, 2017, the entire contents both of which are incorporated herein by reference.

FIELD OF TECHNOLOGY

The following relates to the technical field of medical chemistry, particularly, it relates to a long-acting prodrug of Entecavir and a preparing method as well as use thereof.

BACKGROUND

Entecavir is a new guanosine analogue used to treat hepatitis B virus (HBV) infection, and it is mainly used for treating the adult patients with chronic hepatitis B showing active virus replication, lasting elevation of serum glutamic pyruvic transaminase (ALT) or active lesions in hepatic histology. Entecavir has advantages of high antiviral effect, rapid action, less side-effect, low drug resistance rate in clinical, comparing to previous nucleoside analogue. Entecavir can inhibit HBV efficiently, and has a high genetic barrier for drug resistance. In the treatment of hepatitis B, Entecavir, being used as the first-line antiviral medicament, is a nucleoside analogue which decreases virus fastest and most efficiently with lowest variation ratio. Delayed absorption occurs when Entecavir is administered with food, then $C_{max}$ decreases by 44-46%, and the area under the curve (AUC) of the drug-time curve decreases by 18-20%. Thus, this medicament should be taken on an empty stomach (at least two hours before or after the meal), which brings inconvenience for the patients.

China is hepatitis B widely spread as recognized worldwide. About 130 million people infected with chronic hepatitis B virus, and there are nearly 30 million patients suffers from chronic hepatitis B. According to the latest data, about 500 thousand people die from hepatopathy every year, causing a loss of up to 100 billion yuan to the society.

Hepatitis B is a chronic disease, and long-lasting medicine is required to control the virus level in the body of infected person. Now clinically, Entecavir should be taken once a day, 0.5 mg each time, for the infected adults and teenagers above 16 years old, and the course of treatment may last longer than 6 months according to the illness. Long-acting Entecavir is needed in the market, in order to improve the compliance of patients for taking the medicament, reducing the frequency of taking the medicament, decreasing the possibility of missing the medicament and controlling the virus amount in the patients' body. So far, it is reported for the research direction to focus on improving the targeting for liver and bioavailability, and no long-acting preparation of Entecavir has come into the market. Even none of the improvement in Entecavir directing at the long effectiveness in the field of medical chemistry has been reported. The present disclosure fills the blank in the field.

SUMMARY

An aspect relates to a long-acting prodrug prepared by modifying a structure of Entecavir. The prodrug is insoluble in water, and will be released slowly, sustainably, and steady and converted into Entecavir in the body.

It is a first aspect of the present disclosure to provide a long-acting prodrug of Entecavir, or a stereoisomer, or a pharmaceutically acceptable salt thereof, and the prodrug of Entecavir has a structure of formula

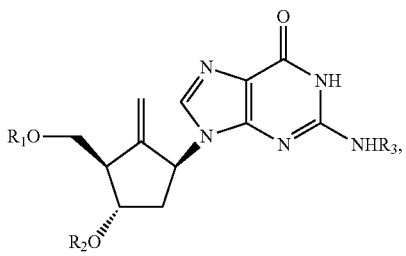

wherein, $R_1$ is selected from H or —C(=O)—$X_1$—$Y_1$; $X_1$ is selected from O, NH, $(CH_2)_m$ or a chemical bond; $Y_1$ is selected from substituted or unsubstituted, branched or linear and saturated or unsaturated $C_{7-30}$ hydrocarbyl, substituted or unsubstituted —NHC(=O)—$C_{7-30}$ hydrocarbyl, substituted or unsubstituted —C(=O)NH—$C_{7-30}$ hydrocarbyl or cholane aliphatic group;

$R_2$ is selected from H or —C(=O)—$X_2$—$Y_2$; $X_2$ is selected from O, NH, $(CH_2)_m$ or a chemical bond; $Y_2$ is selected from substituted or unsubstituted, branched or linear and saturated or unsaturated $C_{9-30}$ hydrocarbyl, substituted or unsubstituted —NHC(=O)—$C_{9-30}$ hydrocarbyl, substituted or unsubstituted —C(=O)NH—$C_{9-30}$ hydrocarbyl or cholane aliphatic group;

$R_3$ is selected from H or —C(=O)—$X_3$—$Y_3$; $X_3$ is selected from O or NH; $Y_3$ is selected from substituted or unsubstituted, branched or linear, and saturated or unsaturated $C_{10-30}$ hydrocarbyl, substituted or unsubstituted —NHC(=O)—$C_{10-30}$ hydrocarbyl, or substituted or unsubstituted —C(=O)NH—$C_{10-30}$ hydrocarbyl;

the substituted hydrocarbyl is optionally substituted with one or more groups independently selected from oxo (=O), thio (=S), halo, amino, —NHC(=O)R, —C(=O)NHR, —C(=O)R, ester group, cycloalkyl, aryl or heteroaryl;

wherein m is an integer from 1 to 6, and R is branched or linear, and saturated or unsaturated $C_1$-$C_{26}$ hydrocarbyl.

Alternatively, $R_1$ is selected from H or —C(=O)—$X_1$—$Y_1$; $X_1$ is selected from O, $(CH_2)_m$ or a chemical bond; $Y_1$ is selected from substituted or unsubstituted, branched or linear and saturated or unsaturated $C_{9-29}$ hydrocarbyl, substituted or =substituted —NHC(O)—$C_{9-29}$ hydrocarbyl, substituted or unsubstituted —C(=O)NH—$C_{9-29}$ hydrocarbyl or cholane aliphatic group.

Alternatively, $R_1$ is selected from H or —C(=O)—$X_1$—$Y_1$; $X_1$ is selected from O, $(CH_2)_m$ or a chemical bond; $Y_1$ is selected from substituted or unsubstituted, branched or linear and saturated or unsaturated $C_{9-27}$ hydrocarbyl, substituted or unsubstituted —NHC(=O)—$C_{9-27}$ hydrocarbyl, substituted or unsubstituted —C(=O)NH—$C_{9-27}$ hydrocarbyl or cholane aliphatic group.

Alternatively, $R_2$ is selected from H or —C(=O)—$X_1$—$Y_2$; $X_2$ is selected from O, $(CH_2)_m$ or a chemical bond; $Y_2$ is selected from substituted or =substituted, branched or linear, and saturated or unsaturated $C_{11-29}$ hydrocarbyl, substituted or unsubstituted —NHC(=O)—$C_{11-29}$ hydrocarbyl, substituted or unsubstituted —C(=O)NH—$C_{11-29}$ hydrocarbyl or cholane aliphatic group.

Alternatively, $R_2$ is selected from H or —C(=O)—$X_2$—$Y_2$; $X_2$ is selected from O, $(CH_2)_m$ or a chemical bond; $Y_2$ is selected from substituted or =substituted, branched or linear and saturated or unsaturated $C_{13-21}$ hydrocarbyl, substituted or unsubstituted —NHC(=O)—$C_{13-21}$ hydrocarbyl, substituted or unsubstituted —C(O)NH—$C_{13-21}$ hydrocarbyl or cholane aliphatic group.

Alternatively, $R_2$ is selected from H or —C(=O)—$X_2$—$Y_2$; $X_2$ is selected from O, $(CH_2)_m$ or a chemical bond; $Y_2$ is selected front substituted or =substituted, branched or linear and saturated or unsaturated $C_{15-17}$ hydrocarbyl, substituted or =substituted —NHC(=O)—$C_{15-17}$ hydrocarbyl, substituted or =substituted —C(=O)NH—$C_{13-17}$ hydrocarbyl or cholane aliphatic group.

Alternatively, $R_3$ is selected from H or —C(=O)—$X_3$—$Y_3$; $X_3$ is selected from O or NH; $Y_3$ is selected from substituted or unsubstituted, branched or linear, and saturated or unsaturated $C_{10-28}$ hydrocarbyl, substituted or unsubstituted —NHC(=O)—$C_{10-28}$ hydrocarbyl, substituted or unsubstituted —C(=O)NH—$C_{10-28}$ hydrocarbyl.

Alternatively, $R_3$ is selected from H or —C(=O)—$X_3$—$Y_3$; $X_3$ is selected from O or NH; $Y_3$ is selected from substituted or unsubstituted, branched or linear, and saturated or unsaturated $C_{11-19}$ hydrocarbyl, substituted or unsubstituted —NHC(=O)—$C_{11-19}$ hydrocarbyl, substituted or unsubstituted —C(=O)NH—$C_{11-19}$ hydrocarbyl.

Alternatively, $R_3$ is selected from H.

Alternatively, m is an integer from 1 to 5, 1 to 4, 1 to 3, 1 or 2.

Alternatively, R is branched or linear, and saturated or unsaturated $C_{1-26}$ hydrocarbyl.

In some embodiments, $R_1$ is selected from H or —C(=O)—$X_1$—$Y_1$; $X_1$ is selected from O, $(CH_2)_m$ or a chemical bond; $Y_1$ is selected from substituted or unsubstituted, branched or linear and saturated or unsaturated $C_{9-29}$ hydrocarbyl, substituted or =substituted —NHC(=O)—$C_{9-29}$ hydrocarbyl, substituted or unsubstituted —C(=O)NH—$C_{9-29}$ hydrocarbyl or cholane aliphatic group;

$R_2$ is selected from H or —C(=O)—$X_2$—$Y_2$; $X_2$ is selected from O, $(CH_2)_m$ or a chemical bond; $Y_2$ is selected from substituted or unsubstituted, branched or linear and saturated or unsaturated $C_{11-29}$ hydrocarbyl, substituted or unsubstituted —NHC(=O)—$C_{11-29}$ hydrocarbyl, substituted or unsubstituted —C(O)NH—$C_{11-29}$ hydrocarbyl or cholane aliphatic group;

$R_3$ is selected from H or —C(=O)—$X_3$—$Y_3$; $X_3$ is selected from O or NH; $Y_3$ is selected from substituted or unsubstituted, branched or linear and saturated or unsaturated $C_{10-28}$ hydrocarbyl, substituted or unsubstituted —NHC(=O)—$C_{10-28}$ hydrocarbyl, substituted or unsubstituted —C(=O)NH—$C_{10-28}$ hydrocarbyl;

the substituted hydrocarbyl is optionally substituted with a substituent selected from O, S, Cl, F, amino, —NHC(=O)R, —C(=O)NHR, —C(=O)R, ester group, cycloalkyl, aryl or heteroaryl;

wherein m is an integer from 1 to 6, and R is branched or linear, and saturated or unsaturated $C_{1-26}$ hydrocarbyl.

In some embodiments, $R_1$ is selected from H or —C(=O)—$X_1$—$Y_1$; $X_1$ is selected from O, $(CH_2)_m$ or chemical bond; $Y_1$ is selected from substituted or unsubstituted, branched or linear and saturated or unsaturated $C_{9-27}$ hydrocarbyl, substituted or unsubstituted —NHC(=O)—$C_{9-27}$ hydrocarbyl, substituted or unsubstituted —C(=O)NH—$C_{9-27}$ hydrocarbyl or cholane aliphatic group;

$R_2$ is selected from H or —C(=O)—$X_2$—$Y_2$; $X_2$ is selected from O, $(CH_2)_m$ or chemical bond; $Y_2$ is selected from substituted or unsubstituted, branched or linear and saturated or unsaturated $C_{13-21}$ hydrocarbyl, substituted or unsubstituted —NHC(=O)—$C_{13-21}$ hydrocarbyl, substituted or unsubstituted —C(=O)NH—$C_{13-21}$ hydrocarbyl or cholane aliphatic group;

$R_3$ selected from H or —C(=O)—$X_3$—$Y_3$; $X_3$ is selected from O or NH; $Y_3$ is selected from substituted or unsubstituted, branched or linear and saturated or unsaturated $C_{11-19}$ hydrocarbyl, substituted or unsubstituted —NHC(=O)—$C_{11-19}$ hydrocarbyl, substituted or unsubstituted —C(=O) NH—$C_{11-19}$ hydrocarbyl;

the substituted hydrocarbyl is optionally substituted with one or more groups independently selected from oxo (=O), thio (=S), Cl, F, amino, —NHC(=O)R, —C(=O)NHR, —C(=O)R, ester group, cycloalkyl, aryl or heteroaryl;

wherein m is an integer from 1 to 6, and R is branched or linear, and saturated or unsaturated $C_{1-26}$ hydrocarbyl.

In some embodiments, $R_1$ is selected from H or —C(=O)—$X_1$—$Y_1$; $X_1$ is selected from O, $(CH_2)_m$ or a chemical bond; $Y_1$ is selected from substituted or =substituted, branched or linear and saturated or unsaturated $C_{9-29}$ hydrocarbyl, substituted or unsubstituted —NHC(=O)—$C_{9-29}$ hydrocarbyl, substituted or unsubstituted —C(O) NH—$C_{9-29}$ hydrocarbyl or cholane aliphatic group;

$R_2$ is selected from H or —C(=O)—$X_2$—$Y_2$; $X_2$ is selected from O, $(CH_2)_m$ or chemical bond; $Y_2$ is selected from substituted or unsubstituted, branched or linear and saturated or unsaturated $C_{15-17}$ hydrocarbyl, substituted or =substituted —NHC(=O)—$C_{15-17}$ hydrocarbyl, substituted or unsubstituted —C(=O)NH—$C_{15-17}$ hydrocarbyl or cholane aliphatic group;

$R_3$ is selected from H;

the substituted hydrocarbyl is optionally substituted with one or more groups independently selected from oxo (=O), thio (=S), Cl, F, amino, —NHC(=O)R, —C(=O)NHR, —C(=O)R, ester group, cycloalkyl, aryl or heteroaryl;

wherein m is an integer from 1 to 6, and R is branched or linear, and saturated or unsaturated $C_{1-26}$ hydrocarbyl.

In some embodiments, when $R_1$ is —C(=O)—$X_1$—$Y_1$, both $R_2$ and $R_3$ are H; when $R_2$ is —C(=O)—$X_2$—$Y_2$, both $R_1$ and $R_3$ are H; and when $R_3$ is —C(O)—$X_3$—$Y_3$, both $R_1$ and $R_2$ are H.

In some embodiments, $R_1$ is —C(=O)—$X_1$—$Y_1$, $X_1$ is O or a chemical bond, $Y_1$ is branched or linear, and saturated or unsaturated $C_{11-25}$ hydrocarbyl, and both $R_2$ and $R_3$ are H.

In some embodiments, $R_1$ is $CH_3$—$(CH_2)_n$—C(=O) NH—$(CH_2)_m$—C(=O)—, wherein n is an integer from 6 to 22, m is an integer from 1 to 6, and both $R_2$ and $R_3$ are H;

Alternatively, $R_1$ is $CH_3$—$(CH_2)_n$—C(=O)NH—$(CH_2)_m$—C(=O)—, wherein n is an integer from 10 to 20, m is an integer from 1 to 3, and both $R_2$ and $R_3$ are H.

In some embodiments, $R_1$ is —C(=O)—X1-Y1, X1 is a chemical bond, and Y1 is selected from one of the following cholane aliphatic groups:

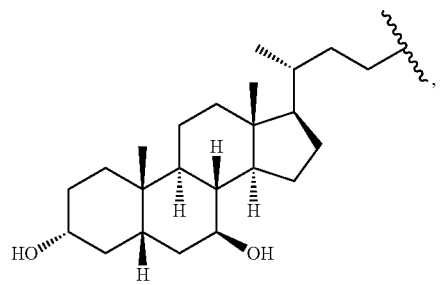

5

-continued

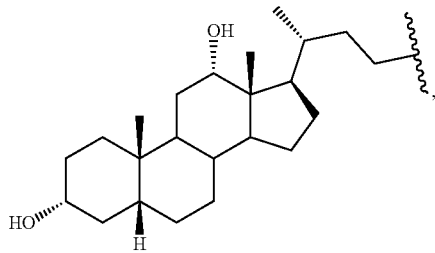

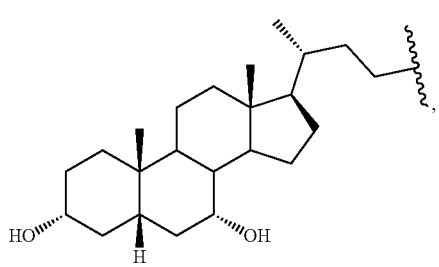

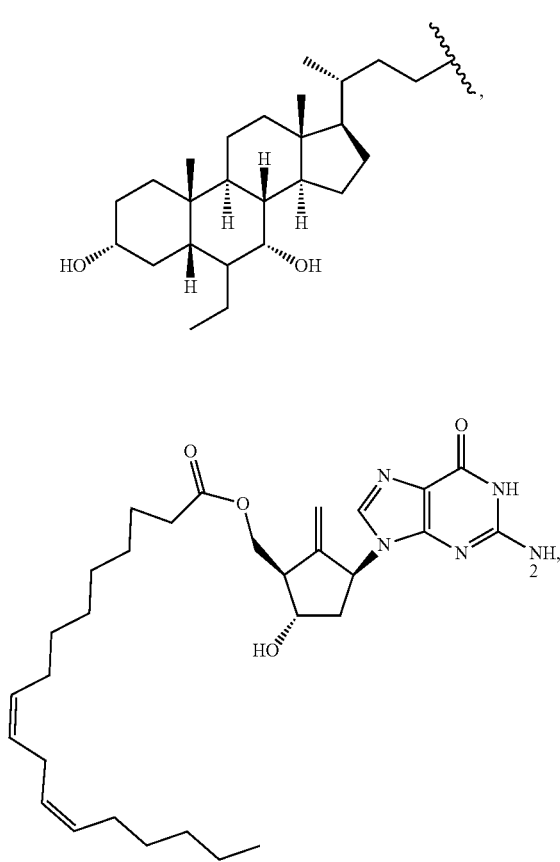

6

-continued

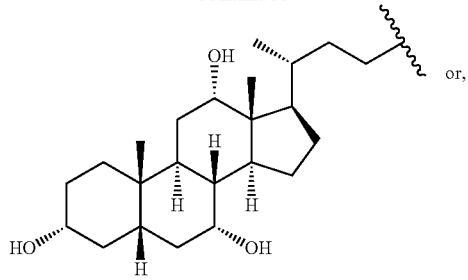

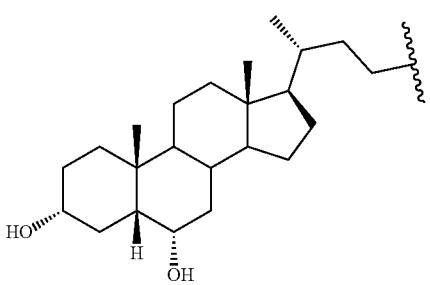

wherein both $R_2$ and $R_3$ are H.

In some embodiments, $R_1$ is alkyl substituted with aryl, alternatively, is alkyl substituted with naphthyl, alternatively, is $C_1$-$C_3$ alkyl substituted with naphthyl.

In some embodiments, $R_2$ is —C(=O)—$X_2$—$Y_2$, $X_2$ is a chemical bond, and $Y_2$ is branched or linear, and saturated or unsaturated $C_{13\text{-}19}$ hydrocarbyl, and both $R_3$ and $R_1$ are H; or $R_3$ is —C(=O)—$X_3$—$Y_3$, $X_3$ is a chemical bond, and $Y_3$ is branched or linear, and saturated or unsaturated. $C_{13\text{-}19}$ hydrocarbyl, and both $R_2$ and $R_1$ are H.

In some embodiments, $R_3$ is —C(=O)—$X_3$—$Y_3$, wherein $X_3$ is O.

In some embodiments, the compound of formula I is selected from one of the following compounds:

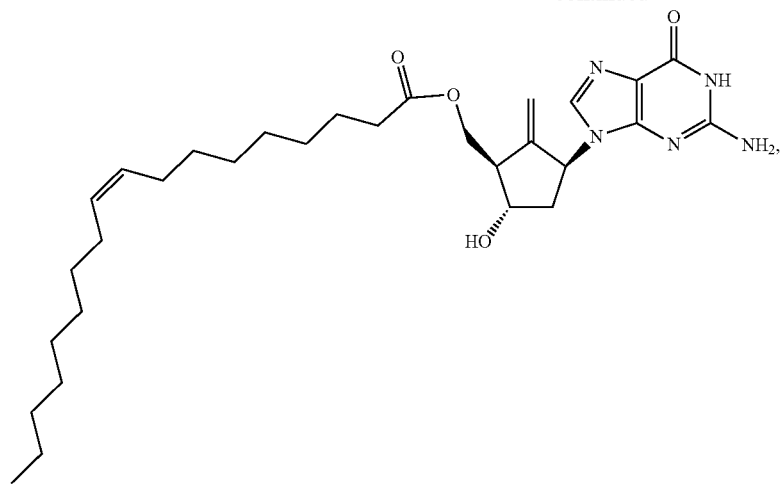
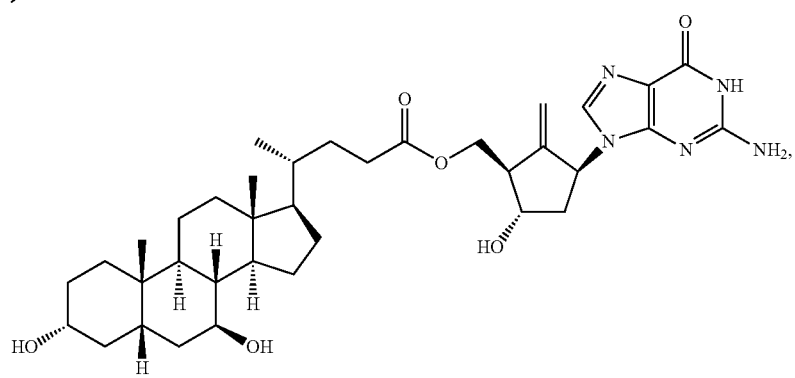
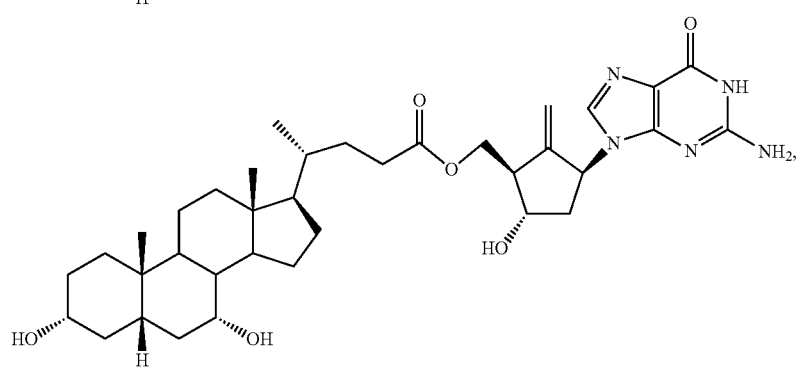
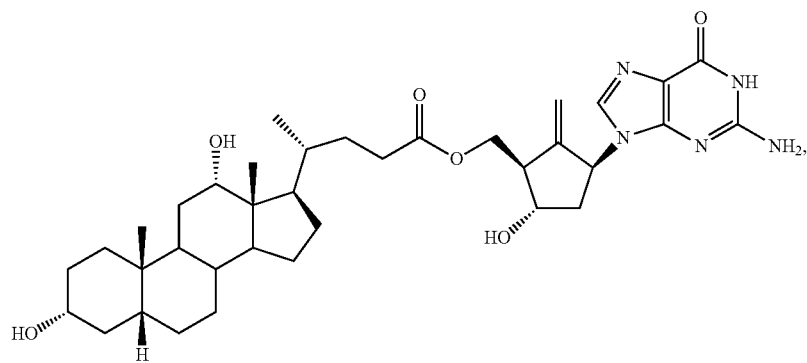

-continued
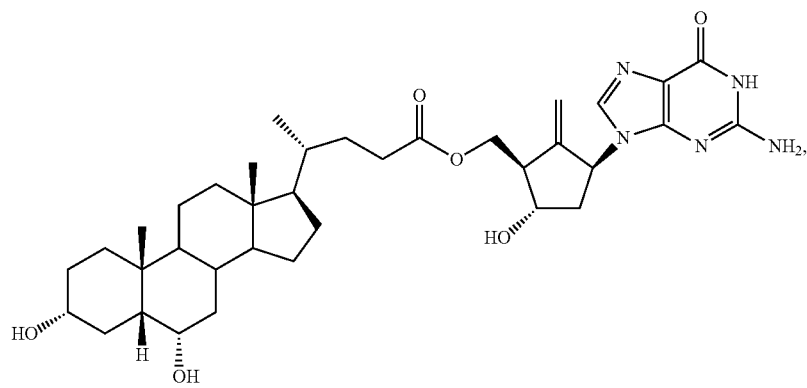
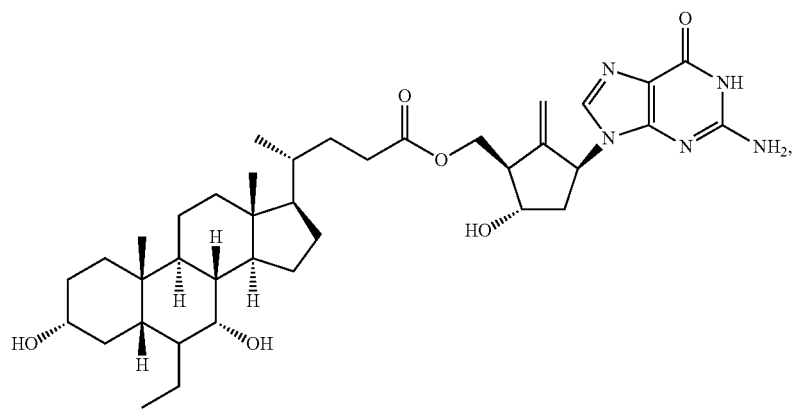
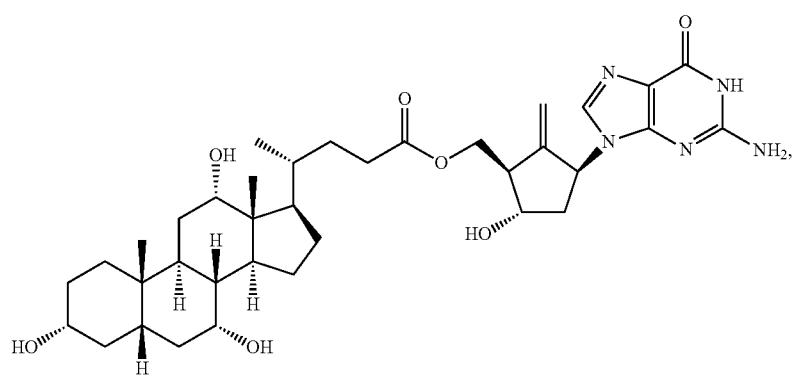
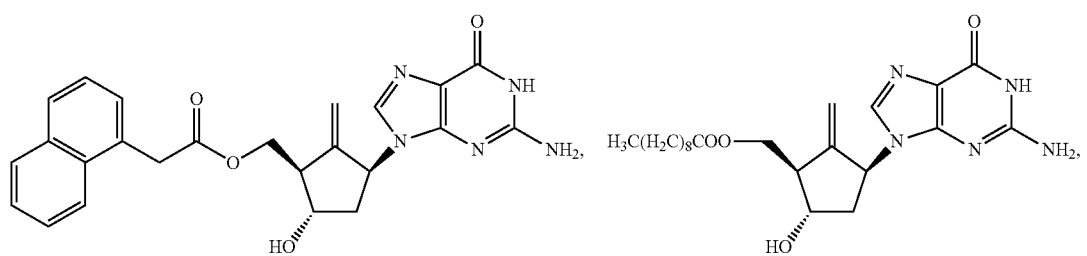
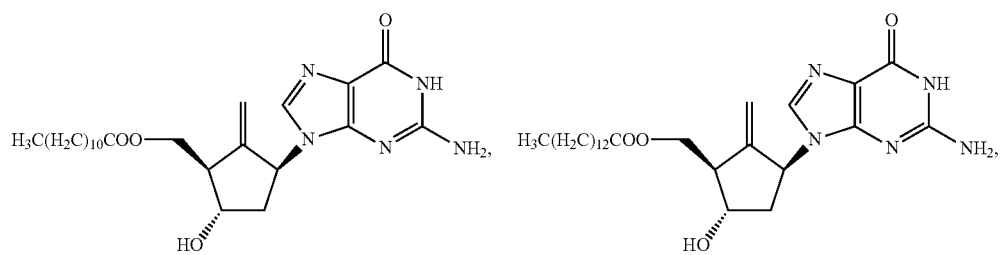

-continued
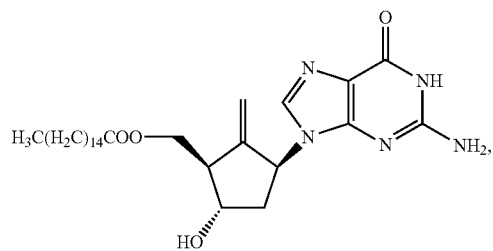
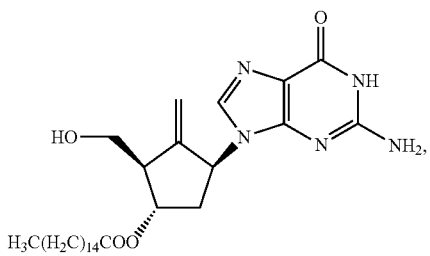
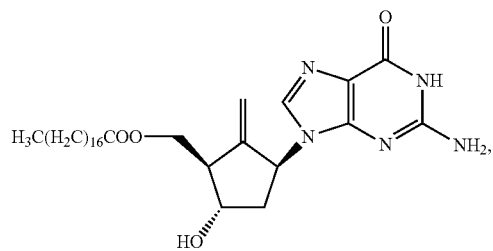
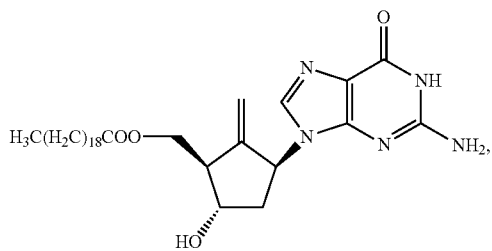
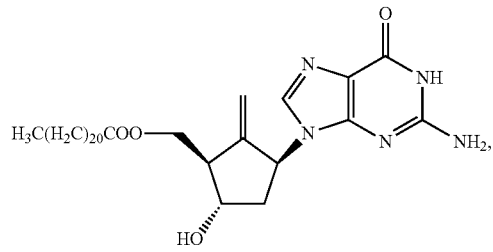
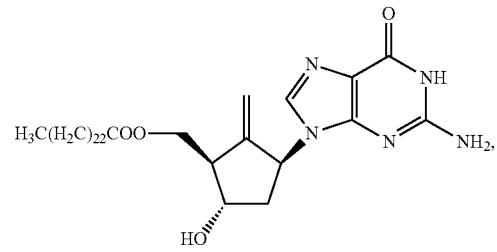
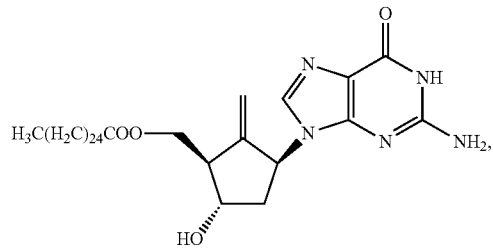
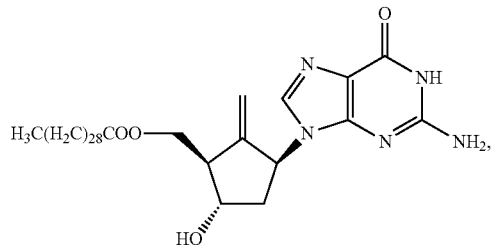
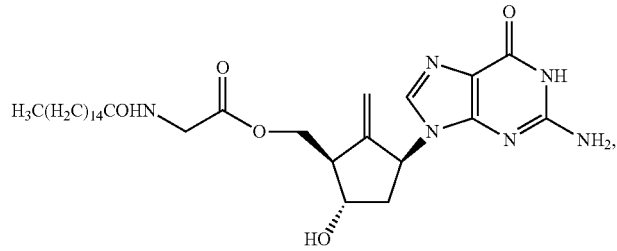
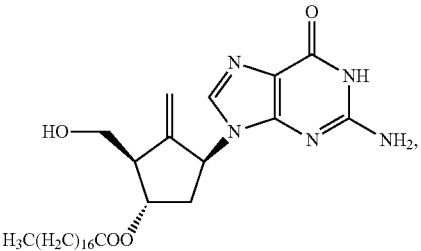
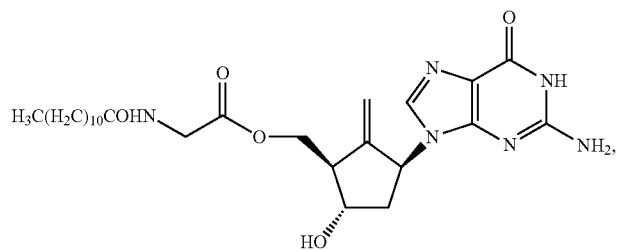

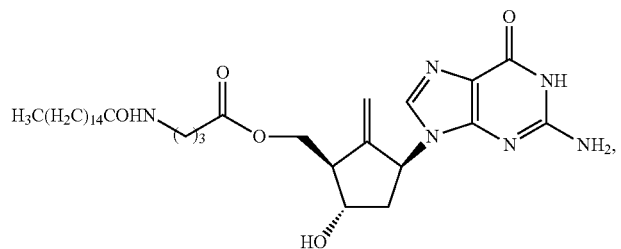
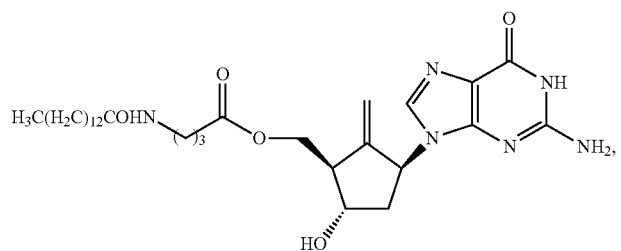
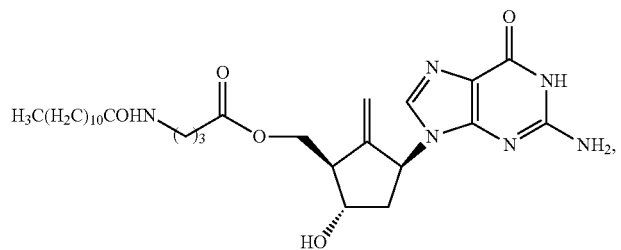
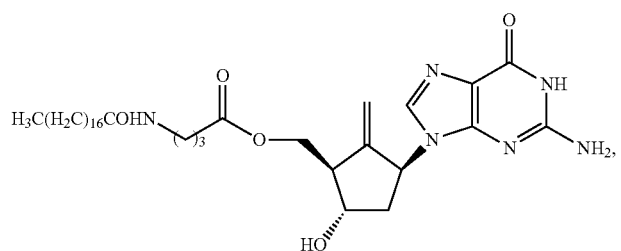
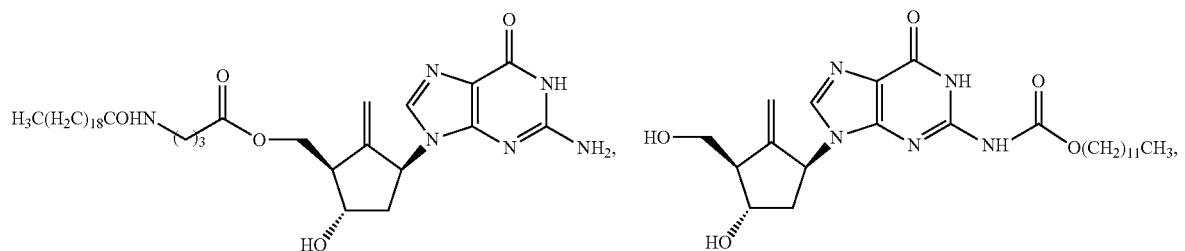
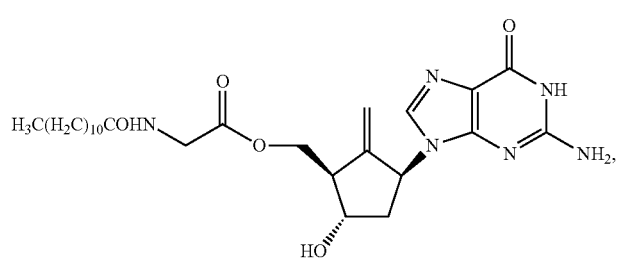

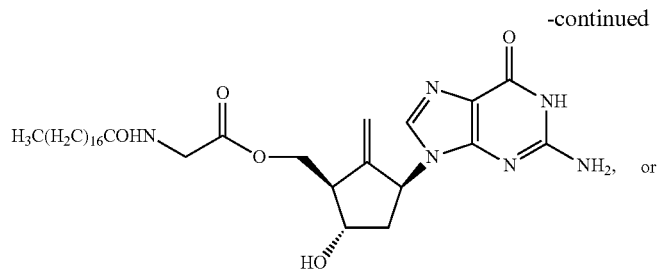 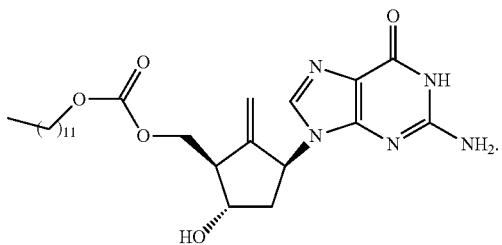

It is another aspect of the present disclosure to provide a method of preparing the prodrug of Entecavir, the method is performed by applying Entecavir or protected Entecavir and organic acid in presence of condensing agent, or by applying Entecavir or protected Entecavir and acyl chloride in presence of organic base acting as an auxiliary acid agent.

The organic acid is selected from the acids corresponding to the acid parts of $R_1$ and $R_2$.

The condensing agent is selected from EDCI, DCC, DIC, CDI, PyBOP, PyBrOP, HATU, HCTU, DEPBT, EEDQ, ethyl chloroformate, isopropyl chloroformate, or isobutyl chloroformate, etc.

The organic base is selected from triethylamine, DIPEA, pyridine, N-methylmorpholine, DBU, etc.

It is another aspect of the present disclosure to provide a pharmaceutical composition, which comprises above-mentioned compound of formula I (prodrug of Entecavir) or a stereoisomer, pharmaceutically acceptable salt and carrier or excipient thereof. Alternatively, the pharmaceutical composition is in a form of solution for injection, suspension for injection or sterile powder for injection.

In some detailed embodiments, the above pharmaceutical composition combines the prodrug of Entecavir with low solubility which is taken as the active ingredients with the suspended solvent and the pharmaceutically acceptable excipient to prepare a suspension which can be injected intramuscularly or subcutaneously. The suspension forms a drug reservoir in the body from which the prodrug is slowly released and digested into active compounds in the body, thereby a long-acting treatment is achieved.

It is another aspect of the present disclosure to provide a use of the foresaid compound (prodrug of Entecavir) of formula I or a pharmaceutically acceptable salt or stereoisomer thereof in the preparation of a medicament for preventing and/or treating a hepatitis B disease. Alternatively, the medicament is a long-acting drug.

Unless stated otherwise or there is an obvious conflict in context, the articles "a," "an," and "said" used herein are intended to include "at least one" or "one or more". Therefore, these articles used herein refer to articles of one or more (i.e., at least one) objects.

The term "comprise" is an open-ended expression, and it includes the content specified in the present disclosure, but does not exclude other aspects.

The term "stereoisomer" refers to compounds having the same chemical structure, but different arrangement of atoms or groups in space. The stereoisomer includes enantiomer, diastereomer, conformer (rotamer), geometric isomer (cis/trans) isomers, atropisomer, etc.

The "enantiomer" refers to two isomers of a compound which are unable to overlap but are mirror images of each other.

The "diastereomer" refers to stereoisomers which have two or more chiral centers and their molecules are not mirror images of each other. The Diastereomer has different physical properties, such as melting points, boiling points, spectral properties, and reactivity. The Diastereomeric mixture can be separated by high resolution analytical operations, for example, electrophoresis and chromatography, such as HPLC.

The term "substitute" refers to replacing a hydrogen in specific structure with a specified substituent. If the substitution on the alkyl or cycloalkyl group is not specified to occur on a specific carbon atom, it may occur on any unsaturated carbon atom. When multiple substituents from the same series are selected, they may be the same or different. If the substitution on benzene ring, heteroaromatic ring, or heterocyclic ring of the present disclosure is not specified to occur on a specific atom, it may occur at any position which are not substituted by other atoms except hydrogen. When multiple substituents from the same series are selected, they may be the same or different. The examples of substituents described herein include, but are not limited to S, O, halogen, amino, hydroxyl, nitryl, azide group, cyanogroup, —NHC(=O)R, —C(=O)NHR, —C(=)R, ester group, cycloalkyl, aryl or heteroaryl, etc, wherein the R is defined as described herein.

The term "unsubstituted" indicates that the specified group does not have any substituent.

In addition, it should be noted that, unless explicitly stated otherwise, the description ways used in the present disclosure such as "each of . . . is independently selected from . . . " and " . . . are each independently selected from" and " . . . are independently" are interchangeable and should be understood in wide sense. It may mean that the specific options among the same symbols in different groups do not affect each other, it also may mean that the specific options among the same symbols in the same group do not affect each other.

In each part of the description of the present disclosure, the substituents of the compounds disclosed in the present disclosure are disclosed according to the type or scope of the group. In particular, the present disclosure includes each independent subcombination of each member of the type and scope of these groups.

In each part of the description of the present disclosure, linking substituents are described. When it is clear that the structure requires a linking group, the Markush variables listed for the group should be understood as a linking group. For example, if the structure requires a linking group and the Markush group for the variable is defined as "alkyl" or "aryl", it should be understood that the "alkyl" or "aryl" respectively represents an attached alkylene or arylene group.

The term "hydrocarbyl" used herein refers to linear, branched or ringed, and saturated or unsaturated group consisting of only hydrogen and carbon atoms, and the group includes aliphatic group and/or aromatic group. The group may include 1, 2, 3, 4, 5, 6, 7, 8, 9, 10, 11, 12, 13, 14, 15, 16, 17, 18, 19 . . . or 30 carbon atoms. Examples of hydrocarbyl include, but are not limited to $C_{1-26}$ alkyl (for example, $C_1$, $C_2$, $C_3$, . . . , or $C_{26}$ alkyl); $C_{7-30}$ alkyl (for example, $C_7$, $C_8$, $C_9$, . . . , or $C_{30}$ alkyl); $C_{9-30}$ alkyl (for example, $C_{10}$, $C_{11}$, . . . , or $C_{30}$ alkyl); $C_{10-30}$ alkyl (for example, $C_{10}$, $C_{11}$, $C_{12}$, . . . , or $C_{30}$ alkyl); $C_{9-29}$ alkyl (for example, $C_9$, $C_{10}$, $C_{11}$, . . . , or $C_{29}$ alkyl); $C_{11-29}$ alkyl (for example, $C_{11}$, $C_{12}$, $C_{13}$, . . . , or $C_{29}$ alkyl); $C_{10-28}$ alkyl (for example, $C_{10}$, $C_{11}$, $C_{12}$, . . . , or $C_{28}$ alkyl); $C_{9-27}$ alkyl (for example, $C_9$, $C_{10}$, $C_{11}$, . . . , or $C_{27}$ alkyl); $C_{13-21}$ alkyl (for example, $C_{13}$, $C_{14}$, $C_{15}$, . . . , or $C_{21}$ alkyl); $C_{11-19}$ alkyl (for example, $C_{11}$, $C_{12}$, $C_{13}$, . . . , or $C_{19}$ alkyl); $C_{7-30}$ alkenyl; $C_{9-30}$ alkenyl; $C_{7-30}$ alkynyl, and $C_{9-30}$ alkynyl. The hydrocarbyl group may be optionally substituted with one or more of substituents described herein.

The term "cycloalkyl" refers to an alkyl with a cyclic structure. For example, $C_3$-$C_{10}$ cyclic alkyl refers to a saturated or unsaturated alkyl with a cyclic structure having 3 to 10 carbon atoms, wherein examples of saturated cyclic alkyl group include, but are not limited to cyclopropyl, cyclopentyl, cyclohexyl, . . . , $C_{10}$ cycloalkyl, and the like, and examples of the unsaturated cyclic alkyl include, but are not limited to, cyclopentene, and the like. The cycloalkyl group may be optionally substituted with one or more of substituents described herein.

The term "aryl" includes aromatic rings having 6, 7, 8, 9, 10, 11, 12, 13, 14, 15 or 16 carbon atoms in the ring. The aryl normally refers to naphthyl, but also may be polycyclic rings with multiple rings, wherein there is at least one aromatic ring.

The term "heteroaryl" includes aromatic rings having 6, 7, 8, 9, 10, 11, 12, 13, 14, 15 or 16 atoms in the ring, and at least one of the atoms in the ring is selected from N, O and S. The group may be polycyclic rings with two or more rings, wherein there is at least one aromatic ring which normally is monocyclic. The term includes groups such as pyrimidinyl, furyl, benzo[b]thienyl, thienyl, pyrryl, imidazolyl, pyrrolidyl, pyridyl, benzo[b]furyl, pyrazinyl, purinyl, indolyl, benzimidazolyl, quinolyl, phenothiazine group, triazinyl, 2,3-diazo naphthyl, 2H-chromenyl, oxazolyl, isoxazolyl, thiazolyl, 4-isoindolyl, indazolyl, purinyl, isoquinolyl, quinazolinyl, pteridyl, etc.

The term "halogen" includes F, Cl, Br, or I. The term "unsaturated" used herein means that a group contains one or more degrees of unsaturation.

The term "prodrug" used herein refers to a compound which is converted into compound of Entecavir in the body. Such convention is affected by hydrolysis of prodrug in the blood or the prodrug being converted into the parent structure in the blood or tissues in presence of enzymes. Compared to the conventional art, the present disclosure has the following benefits:

the prodrug of Entecavir of the present disclosure has a low solubility, and it can be made into an injection and form a drug reservoir in the body after the administration, prolonging the release time of the drug in the body, and achieving an effect of long-acting treatment.

BRIEF DESCRIPTION OF DRAWINGS

Some of the examples will be described in detail, with reference to the following figures, wherein like designations denote like members, where.

DETAILED DESCRIPTION

Figure 1:
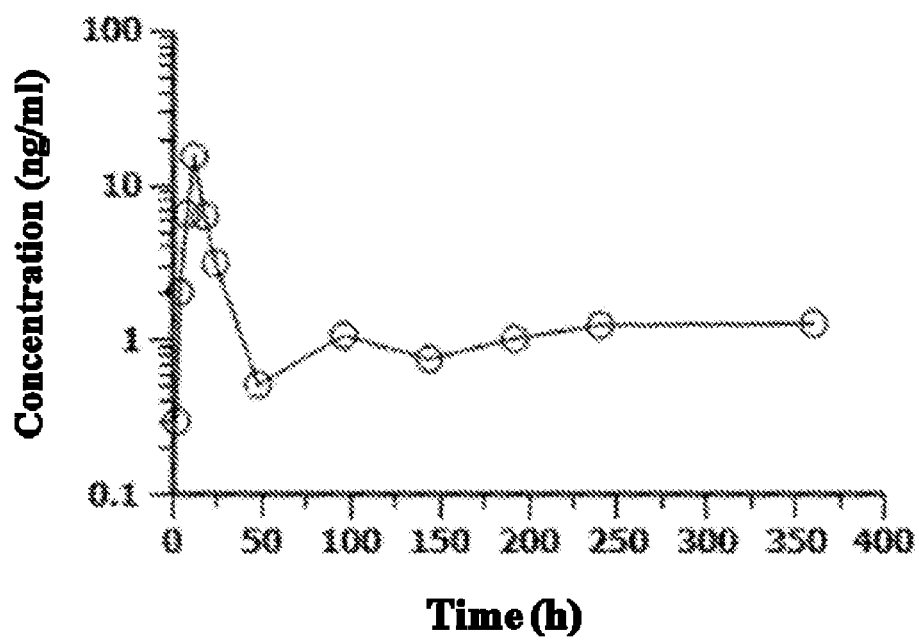
FIG. 1 shows a change of blood concentration of Entecavir after Entecavir-5'-docosanoate was administered to a beagle.

The present disclosure will be further described by the following examples. However, the examples are not intended to limit the protection scope of the present disclosure.

Example 1 Preparation of Entecavir-5'-palmitate

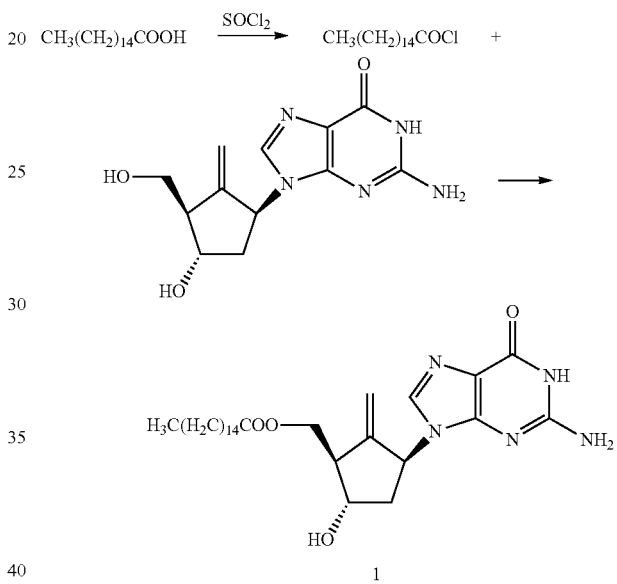

690 mg of palmitic acid was added to 5 mL of sulfoxide chloride in a 50 mL single-neck flask, and heated to 78° C. followed by stirring and reacting for 1 to 2 hours. After the reaction, a concentration was performed to dryness under reduced pressure, then 5 mL of DCM was added. Further concentration was performed under reduced pressure while an oil pump was used to vacuumize for 1 hour, and acyl chloride was obtained for later use. 500 mg of Entecavir was added into 10 mL of pyridine, and DMAP in catalytic amount was further added. After the temperatures was lowered to 0° C., the obtained acyl chloride was dropwise added into the reaction flask. Half an hour after the stirring and reaction was started, the temperature was raised to room temperature, and stirring was kept with the reaction overnight.

After the reaction was finished, water and dichloromethane were used for extraction, and saturated sodium bicarbonate and sodium chloride were successively used to wash. Organic phase was dried by anhydrous sodium sulfate, and concentrated to dryness under reduced pressure. Column chromatography was performed, wherein dichloromethane and methanol (volume ratio from 20:1 to 10:1) were used for gradient elution, and the elution part at a volume ratio of 10:1 was collected so as to obtain 105 mg of compound 1 of Entecavir-5'-palmitate, with a yield of 11.29%.

¹H NMR (400 MHz, DMSO-d6) δ 10.66 (s, 1H), 7.65 (s, 1H), 6.47 (s, 2H), 5.44-5.33 (m, 1H), 5.14 (s, 1H), 5.10 (d, J=2.8 Hz, 2H), 4.63 (s, 1H), 4.18 (m, 3H), 2.74 (s, 1H), 2.32 (m, 3H), 2.15-2.03 (m, 1H), 1.59-1.45 (m, 2H), 1.21 (s, 24H), 0.84 (t, J=6.8 Hz, 3H).

Example 2 Preparation of Entecavir-5'-stearate

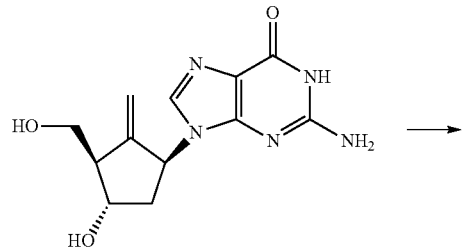

The process step was performed with reference to the method of Example 1, except that the palmitic acid was replaced with stearic acid. After the reaction product was separated and purified, the compound 2 of Entecavir-5'-stearate was obtained, with a yield of 25.50%.

¹H NMR (400 MHz, DMSO-d6) δ 10.65 (s, 1H), 7.66 (s, 1H), 6.47 (s, 2H), 5.43-5.33 (m, 1H), 5.15 (s, 1H), 5.10 (d, J=3.2 Hz, 1H), 4.62 (s, 1H), 4.18 (m, 3H), 2.74 (s, 1H), 2.36-2.24 (m, 3H), 2.13-2.04 (m, 1H), 1.58-1.49 (m, 2H), 1.23 (s, 28H), 0.84 (t, J=6.8 Hz, 3H).

Example 3 Preparation of Entecavir-5'-icosanoate

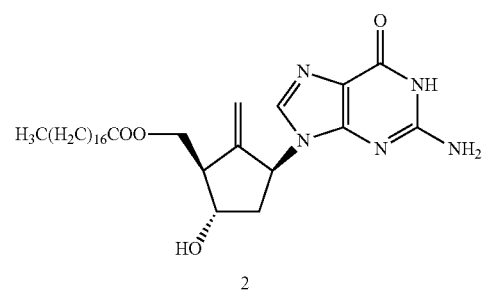

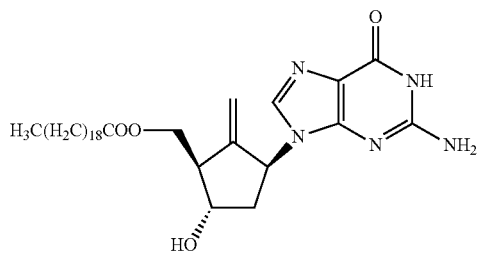

The process step was performed with reference to the method of Example 1, except that the palmitic acid was replaced with icosanoic acid. After the reaction product was separated and purified, the compound 3 of Entecavir-5'-icosanoate was obtained, with a yield of 29.10%.

¹H NMR (400 MHz, DMSO-d6) δ 10.58 (s, 1H), 7.66 (s, 1H), 6.47 (s, 2H), 5.38 (m, 1H), 5.15 (s, 1H), 5.08 (d, J=3.2 Hz, 1H), 4.62 (s, 1H), 4.18 (m, 3H), 2.73 (s, 1H), 2.34-2.25 (m, 3H), 2.15-2.01 (m, 1H), 1.63-1.46 (m, 2H), 1.23 (s, 32H), 0.85 (t, J=6.8 Hz, 3H).

Example 4 Preparation of Entecavir-5'-docosanoate

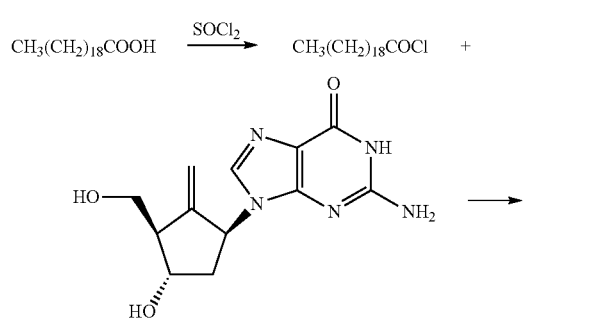

The process step was performed with reference to the method of Example 1, except that the palmitic acid was replaced with docosanoic acid. After the reaction product was separated and purified, the compound 4 of Entecavir-5'-docosanoate was obtained, with a yield of 30.50%.

¹H NMR (400 MHz, DMSO-d6) δ 10.58 (s, 1H), 7.66 (s, 1H), 6.41 (s, 2H), 5.38 (t, J=8.9 Hz, 1H), 5.15 (s, 1H), 5.08 (d, J=3.2 Hz, 1H), 4.62 (s, 1H), 4.18 (m, 3H), 2.70 (d, J=23.4 Hz, 1H), 2.38-2.25 (m, 3H), 2.15-2.00 (m, 1H), 1.59-1.45 (m, 2H), 1.22 (s, 36H), 0.85 (t, J=6.7 Hz, 3H).

Example 5 Preparation of Entecavir-5'-ursodesoxycholate

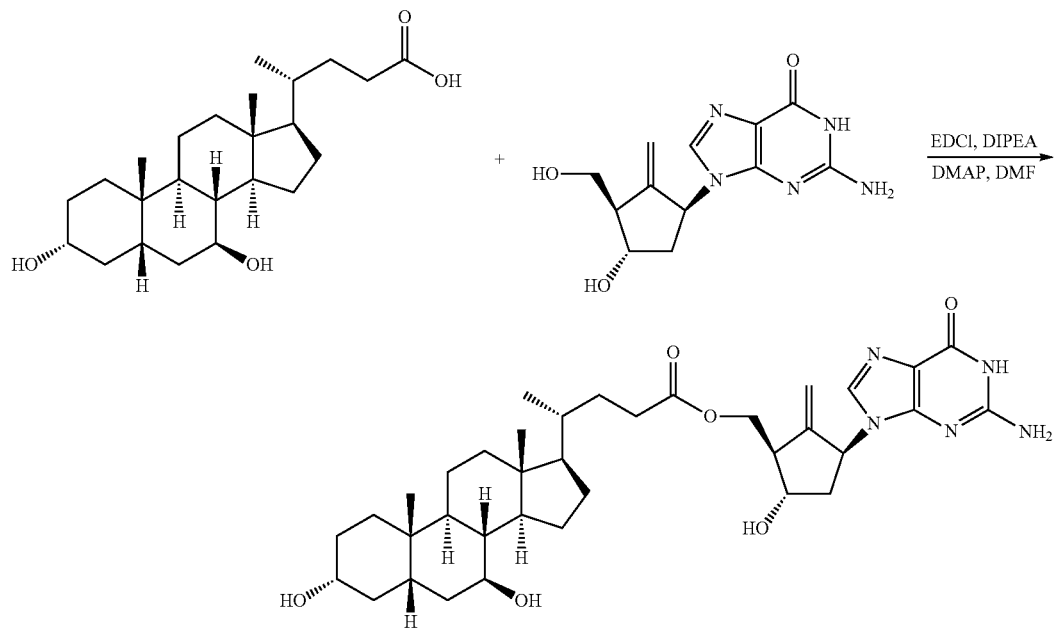

710 mg of ursodesoxycholic acid, 500 mg of Entecavir, 350 mg of EDCI, 0.3 mL DIPEA, and DMAP in catalytic amount were dissolved in 90 mL of DMF in a 250 mL single-neck flask, stirred and reacted for 18 hours. TLC test showed that half of the materials were reacted. Stirring was continued until the reaction finished.

1 mL of methanol was added for quenching reaction for 1 hour, and water and DCM were added to extract after the reaction. Solid dissoluble in methanol was precipitated and collected. TLC was used to test the solid, organic phase and aqueous phase, and it was shown that the product was mainly in the solid phase. After the solid phase was evaporated to dryness, column chromatography was performed, wherein dichloromethane and methanol (volume ratio from 10:1 to 7:1) were used for gradient elution, and the elution part at a volume ratio of 7:1 was collected so as to obtain 300 mg of compound 5 of Entecavir-5'-ursodesoxycholate, with a yield of 25.53%.

$^1$H NMR (500 MHz, DMSO-d6) δ 10.59 (s, 1H), 7.66 (s, 1H), 6.41 (s, 2H), 5.37 (t, J=9.1 Hz, 1H), 5.15 (s, 1H), 5.07 (d, J=32 Hz, 1H), 4.61 (s, 1H), 4.43 (d, J=4.6 Hz, 1H), 4.17 (m, 3H), 3.86 (d, J=6.8 Hz, 1H), 3.31-3.23 (m, 2H), 2.73 (s, 1H), 2.42-2.20 (m, 3H), 2.12-2.03 (m, 1H), 1.92 (d, J=11.6 Hz, 1H), 1.88-1.77 (m, 1H), 1.77-1.59 (m, 4H), 1.47-1.34 (m, 18H), 0.89 (d, J=6.5 Hz, 4H), 0.86 (s, 3H), 0.60 (s, 3H).

Example 6 Preparation of Entecavir-5'-oleate

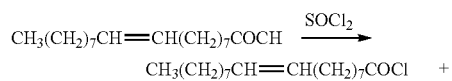

CH$_3$(CH$_2$)$_7$CH=CH(CH$_2$)$_7$COCH $\xrightarrow{SOCl_2}$
CH$_3$(CH$_2$)$_7$CH=CH(CH$_2$)$_7$COCl +

-continued

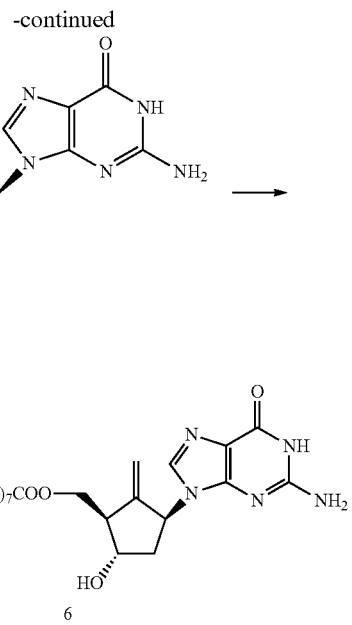

The process step was performed with reference to the method of Example 1, except that the palmitic acid was replaced with oleic acid. After the reaction product was separated and purified, the compound 6 of Entecavir-5'-oleate was obtained, with a yield 21.98%.

$^1$H NMR (400 MHz, DMSO-d6) δ 10.86 (s, 1H), 7.64 (s, 1H), 6.70 (s, 2H), 5.44-5.24 (m, 3H), 5.23-5.09 (m, 2H), 4.60 (t, J=2.3 Hz, 1H), 4.25-4.09 (m, 3H), 2.71 (s, 1H), 2.38-2.22 (m, 3H), 2.08 (m, 1H), 1.98 (m, 4H), 1.51 (m, 2H), 1.38-1.11 (m, 20H), 0.84 (t, J=6.9 Hz, 3H).

Example 7 Preparation of Entecavir-5'-naphthylacetate

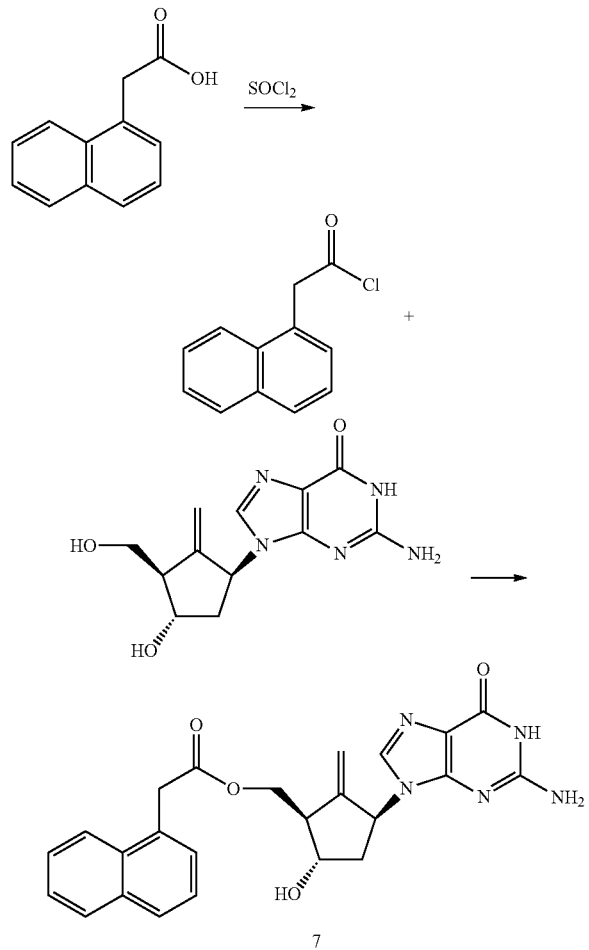

The process step was performed with reference to the method of Example 1, except that the palmitic acid was replaced with naphthylacetic acid. After the reaction product was separated and purified, the compound 7 of Entecavir-5'-naphthylacetate was obtained, with a yield of 18.85%.

$^1$H NMR (400 MHz, DMSO-d6) δ 10.81 (br, 1H), 7.94 (dt, J=6.7, 2.4 Hz, 2H), 7.85 (dd, J=6.3, 3.3 Hz, 1H), 7.56 (s, 1H), 7.52 (dt, J=6.5, 3.6 Hz, 2H), 7.48-7.42 (m, 2H), 6.65 (s, 2H), 5.33 (t, J=9.3 Hz, 1H), 5.17 (d, J=3.2 Hz, 1H), 5.00 (t, J=2.4 Hz, 1H), 4.50 (t, J=2.5 Hz, 1H), 4.28-4.13 (m, 4H), 4.10 (s, 1H), 2.80-2.69 (m, 1H), 2.14 (td, J=12.0, 11.4, 4.9 Hz, 1H), 2.06-1.90 (m, 1H).

Example 8 Preparation of Entecavir-5'-palmitoylaminoacetate

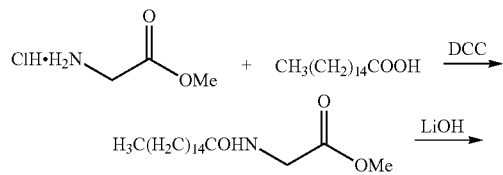

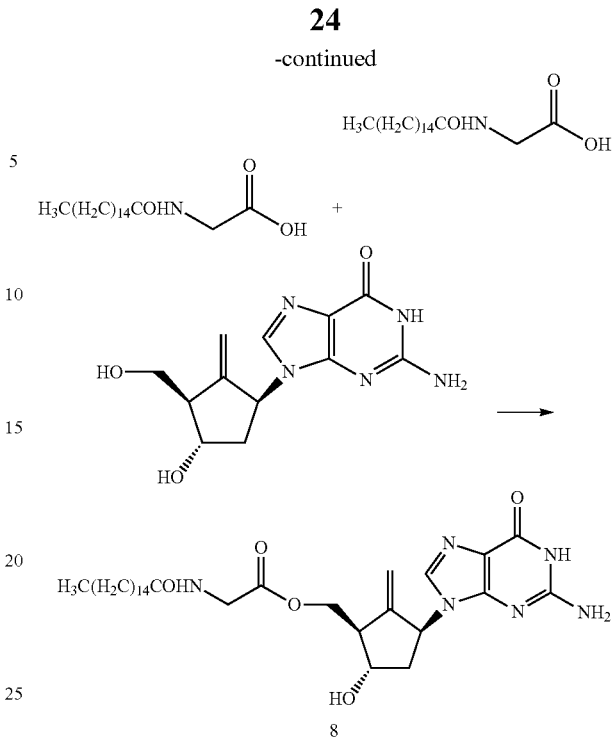

Methyl aminoacetate hydrochloride (0.73 g), palmitic acid (1 g), DCC (1.21 g) and DMAP (95 mg) were added into 50 mL single-neck flask. Then 20 mL of THF and 1.51 g of DIPEA were added and stirred at room temperature overnight. Filtrate was collected after filtration, and rotated to dryness. DCM was added to dissolve, and water, dilute HCl, saturated sodium bicarbonate and saturated saline solution were successively used to wash. Anhydrous sodium sulfate was used for drying, followed by filtration and rotation to dryness. Methanol was used for recrystallization, and 0.35 g of methyl palmitoylaminoacetate was obtained.

The 0.35 g of palmitoylaminoacetate was dissolved in 10 mL of THF, and 50 mg of lithium hydrate monohydrate was dissolved in 5 mL of water. The lithium hydrate solution was dropwise added and stirred at room temperature for 2 hours, then the reaction was terminated. Dilute HCl was added to adjust pH to 1~2 so as to precipitate solid, after the filtration and drying, the palmitoylaminoacetate was obtained.

88 mg of Entecavir and 100 mg of palmitoylaminoacetate were added into 50 mL single-neck flask, and 10 mL of DMF was added to dissolve. EDCI (612 mg), HOBT (431 mg), and TEA (0.44 mL) were added and stirred at room temperature overnight. After the rotation to dryness, DCM was added to dissolve, and dilute HCl, saturated sodium bicarbonate and saturated saline solution were successively used to wash. Anhydrous sodium sulfate was used for drying, followed by filtration and rotation to dryness. Column chromatography isolation was performed, then 43 mg of compound 8 of Entecavir-5'-palmitoylaminoacetate was obtained with a yield of 23.63%.

$^1$H NMR (400 MHz, DMSO-d6) δ 10.66 (s, 1H), 7.65 (s, 1H), 6.47 (s, 2H), 5.44-5.33 (m, 1H), 5.19-5.05 (in, 2H), 4.63 (s, 1H), 4.18 (dt, J=6.5, 4.0 Hz, 3H), 3.61 (s, 2H), 3.08 (d, J' 7.3 Hz, 1H), 2.74 (s, 1H), 2.32 (t, J=7.3 Hz, 3H), 2.15-2.03 (m, 1H), 1.59-1.45 (m, 2H), 1.21 (d, J=10.2 Hz, 28H), 0.84 (s, 3H).

Example 9 Preparation of Entecavir-3'-palmitate

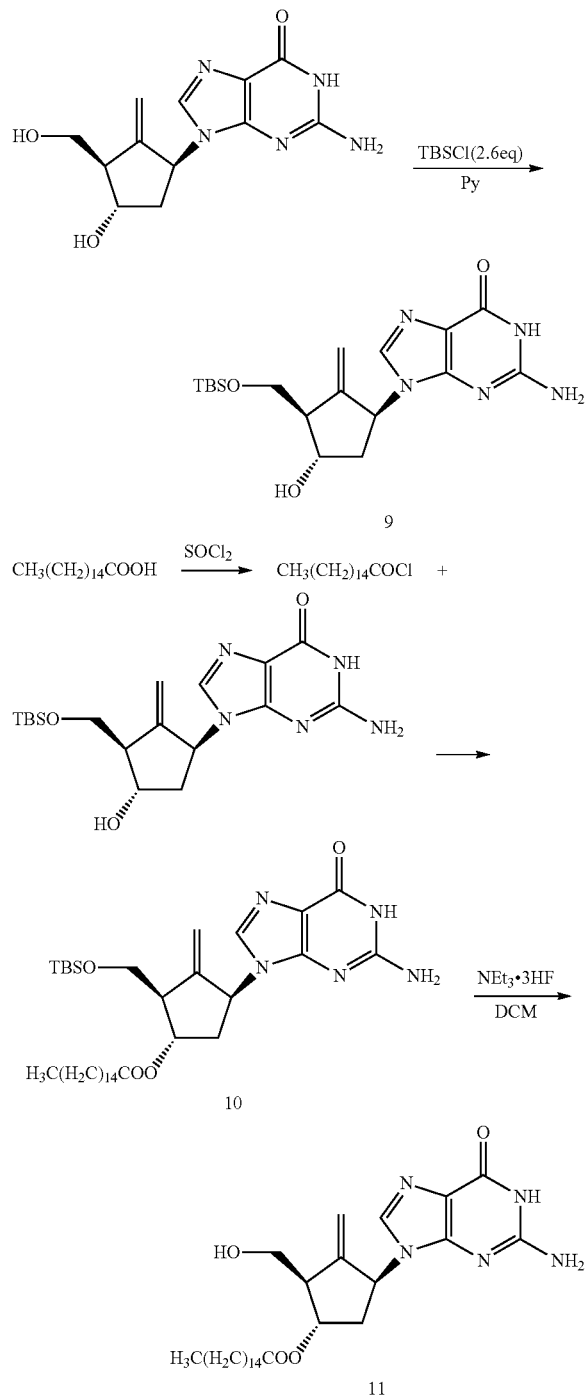

was performed to dryness under reduced pressure, and column chromatography isolation was performed to obtain 0.8 g of compound 9.

167 mg of palmitic acid was added to 1 mL of sulfoxide chloride in 50 mL single-neck flask, and heated to 78° C., After stirring and reaction for 1 to 2 hours, the reaction was finished. A concentration was performed to dryness under reduced pressure, and 5 mL of DCM was added. Further concentration was performed under reduced pressure while an oil puny was used to vacuumize for 1 hour, and acyl chloride was obtained for later use. 200 mg of compound 9 was added into 10 mL of pyridine, and DMAP in catalytic amount was further added. After the temperatures was lowered to 0° C., the obtained acyl chloride was dropwise added into the reaction flask. Half an hour after the stirring and reaction was started, the temperature was raised to room temperature, and stirring was kept with the reaction overnight. After the post-processing reaction was finished, water and dichloromethane were used for extraction, and saturated sodium bicarbonate and sodium chloride were used to wash. Organic phase was dried by anhydrous sodium sulfate, and concentrated to dryness under reduced pressure, so as to obtain 350 mg of compound 10.

350 mg of compound 10 was dissolved in 5 mL of DCM, and 266 mg of triethylamine trifluoride was added and kept stirring at room temperature overnight. Saturated sodium bicarbonate and saline solution were successively used to wash. The organic phase was dried by anhydrous sodium sulfate and concentrated to dryness under reduced pressure. Column chromatography was performed, wherein dichloromethane and methanol (volume ratio from 30:1 to 10:1) were applied, and the elution part at a volume ratio of 10:1 was collected and concentrated, so as to obtain 130 mg of compound 11 of Entecavir-3'-palmitate, with a yield of 28.00%.

$^1$H NMR (500 MHz, DMSO-d6) δ10.61 (s, 1H), 7.70 (s, 1H), 6.43 (s, 2H), 5.25-5.26 (m, 2H), 5.16 (s, 1H), 5.00 (t, J=5.0 Hz, 1H), 4.61 (s, 1H), 3.62 (t, J=5.7 Hz, 2H), 2.67 (s, 1H), 2.50 (m, 1H), 2.28 (t, J=7.3) Hz, 2H), 2.19 (m, 1H), 1.58-1.46 (m, 2H), 1.22 (d, J=13.2 Hz, 24H), 0.84 (t, J=6.9 Hz, 3H).

Example 10 Preparation of Entecavir-3'-stearate

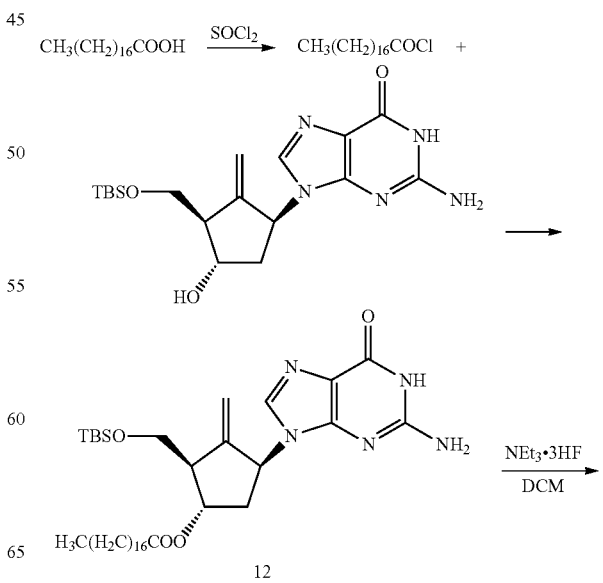

1 g of Entecavir was dissolved in 10 mL of pyridine, and 1.4 g of (2.4 eq) TBSCl was added and stirred to react for 2 hours. TLC test showed that the materials basically disappeared, two points appeared. Methanol was added to terminated the reaction, and water and DCM are used to extract. Saturated sodium bicarbonate and saturated sodium chloride were used to wash the organic phase and anhydrous sodium sulfate was used to dry the solution. A concentration -continued

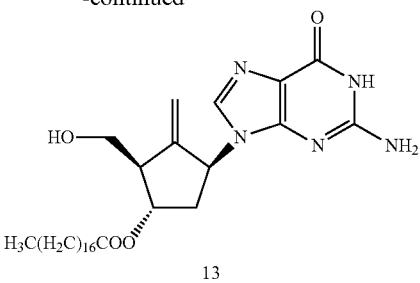

13

The process step was performed with reference to the method of Example 9, except that the palmitic acid was replaced with stearic acid. After the reaction product was separated and purified, the compound 13 of Entecavir-3'-stearate was obtained, with a yield of 22.44%.

$^1$H NMR (500 MHz, DMSO-d6) δ 10.59 (s, 1H), 7.70 (s, 1H), 6.42 (s, 2H), 5.27 (m, 2H), 5.16 (s, 1H), 4.99 (t, J=4.9 Hz, 1H), 4.61 (s, 1H), 3.62 (t, J=5.2 Hz, 2H), 2.67 (s, 1H), 2.50 (m, 1H), 2.29 (d, J=7.0 Hz, 2H), 2.19 (m, 1H), 1.52 (s, 2H), 1.22 (s, 28H), 0.84 (t, J=6.3 Hz, 3H).

Example 11 Preparation of Entecavir-2-dodecylcarbamate

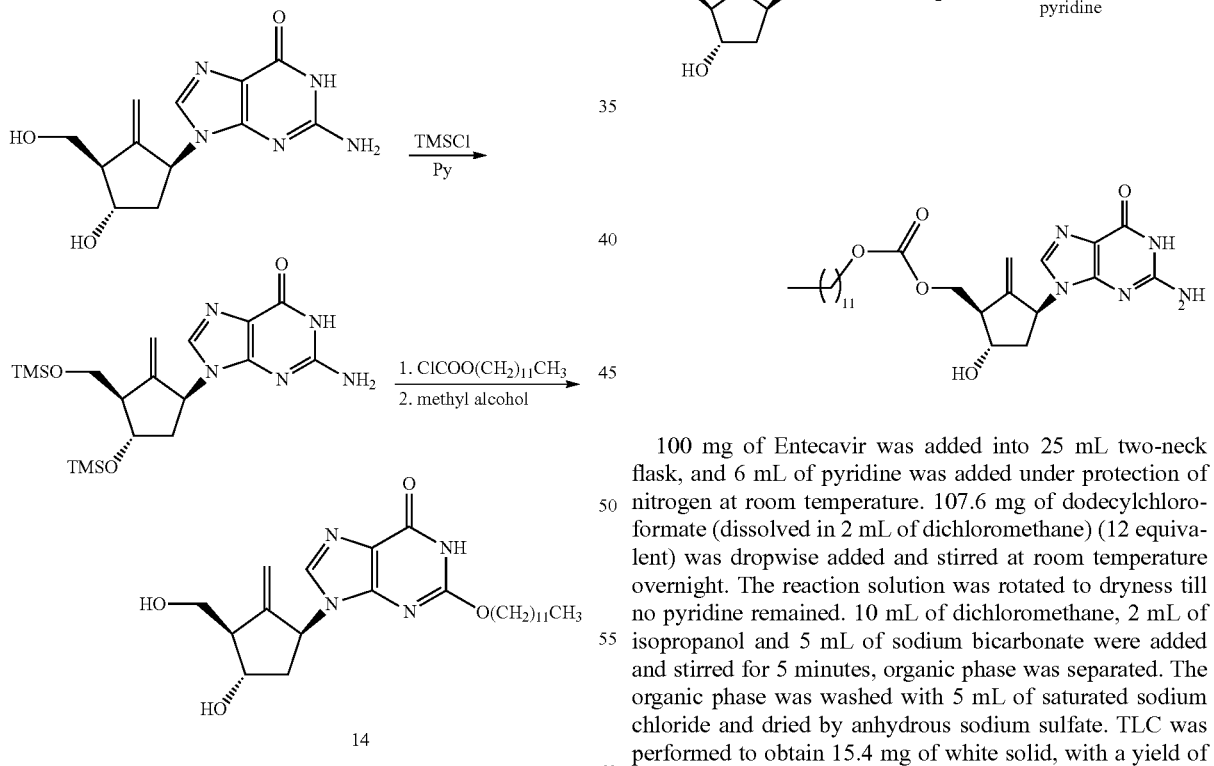

400 mg of Entecavir, 10 mL of pyridine and 0.67 mL of TMSCl were successively added into 50 mL single-neck flask, stirred for 3 hours. TLC test showed that the materials were basically reacted. 0.6 mL of dodecyl chloroformate was added and stirred overnight, then the reaction was finished.

1 mL of methanol was added for quenching reaction, heated to 45° C. and stirred for reaction for 1 hour. Dichloromethane and water were added to extract after the reaction, and the organic phase was extracted successively by saturated sodium bicarbonate and sodium chloride. The organic phase was dried by anhydrous sodium sulfate and concentrated to dryness. Column chromatography was performed, wherein dichloromethane and methanol (volume ratio from 8:1 to 5:1) were used for gradient elution, and the elution part at a volume ratio of 5:1 was collected and concentrated, so as to obtain 200 mg of compound 14 of Entecavir-2-dodecylcarbamate, with a yield of 18.41%.

$^1$H NMR (500 MHz, DMSO-d6) δ 11.35 (br, 1H), 7.93 (s, 1H), 5.44 (t, J=8.9 Hz, 1H), 5.10 (s, 1H), 4.93 (s, 1H), 4.86 (s, 1H), 4.53 (s, 1H), 4.26 (s, 1H), 4.15 (t, J=6.3 Hz, 2H), 3.54 (s, 2H), 2.54 (s, 1H), 2.31 (m, 1H), 2.12-2.04 (m, 1H), 1.61 (t, J=6.7 Hz, 2H), 1.32 (d, J=6.5 Hz, 2H), 1.23 (s, 18H), 0.84 (t, J=6.7 Hz, 3H).

Example 12 Preparation of Entecavir-2-dodecylcarbonate 100 mg of Entecavir was added into 25 mL two-neck flask, and 6 mL of pyridine was added under protection of nitrogen at room temperature. 107.6 mg of dodecylchloroformate (dissolved in 2 mL of dichloromethane) (12 equivalent) was dropwise added and stirred at room temperature overnight. The reaction solution was rotated to dryness till no pyridine remained. 10 mL of dichloromethane, 2 mL of isopropanol and 5 mL of sodium bicarbonate were added and stirred for 5 minutes, organic phase was separated. The organic phase was washed with 5 mL of saturated sodium chloride and dried by anhydrous sodium sulfate. TLC was performed to obtain 15.4 mg of white solid, with a yield of 8.72%.

$^1$H NMR (400 MHz, DMSO-d6) δ10.65 (br, 1H), 7.65 (s, 1H), 6.47 (s, 2H), 5.43-5.33 (m, 1H), 5.16 (s, 1H), 5.12 (d, J=2.8 Hz, 1H), 4.62 (s, 1H), 4.30-4.19 (m, 2H), 4.16 (s, 1H), 4.09 (t, J=6.8 Hz, 2H), 2.77 (s, 1H)), 2.31 (ddd, J=12.6, 10.5, 4.7 Hz, 1H), 2.13-2.03 (m, 1H), 1.59 (p, J=6.8 Hz, 2H), 1.25 (m, 18H), 0.85 (t, J=6.8 Hz, 3H).

Example 13 Preparation of Entecavir-5'-hexacosanate

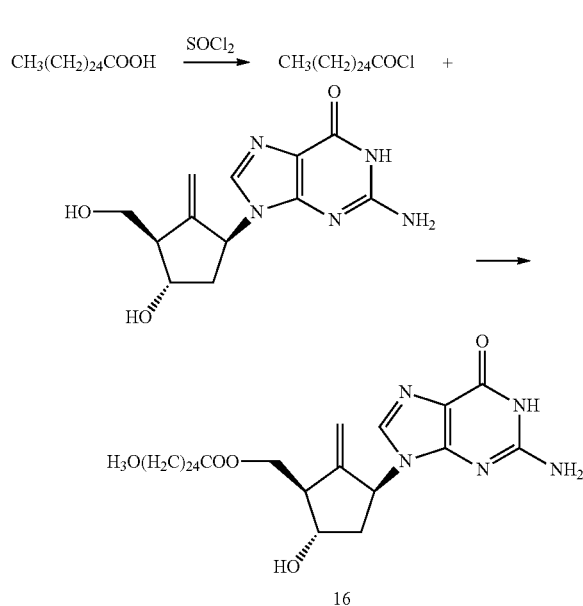

The process step was performed with reference to the method of Example 1, except that the palmitic acid was replaced with hexacosanic acid. After the reaction product was separated and purified, the compound 16 of Entecavir-5'-hexacosanate was obtained, with a yield of 21.33%.

$^1$H NMR (400 MHz, DMSO-d6) δ 10.58 (s, 1H), 7.66 (s, 1H), 6.40 (s, 2H), 5.38 (d, J=8.9 Hz, 1H), 5.14 (s, 1H), 5.08 (d, J=3.2 Hz, 1H), 4.62 (s, 1H), 4.18 (m, 3H), 2.73 (d, J=23.4 Hz, 1H), 2.34-2.26 (m, 3H), 2.10-2.05 (m, 1H), 155-1.51 (m, 2H), 1.22 (s, 44H), 0.85 (t, J=6.7 Hz, 3H).

Example 14 Preparation of Entecavir-5'-triacontanate

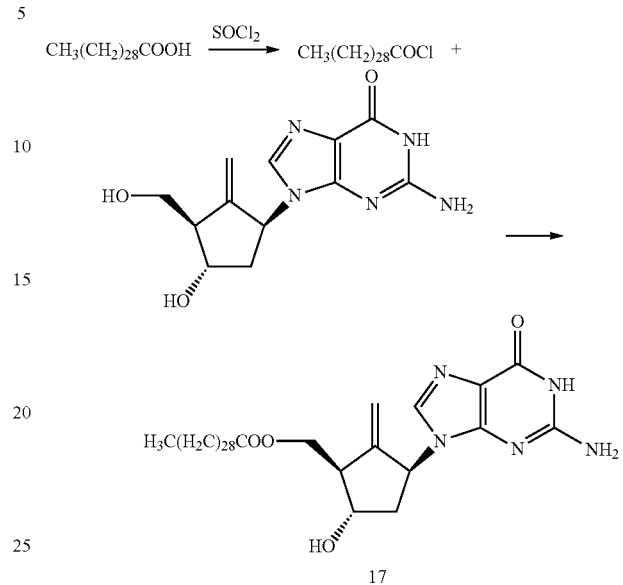

The process step was performed with reference to the method of Example 1, except that the palmitic acid was replaced with triacontanic acid. After the reaction product was separated and purified, the compound 17 of Entecavir-5'-triacontanate was obtained, with a yield of 16.59%.

$^1$H NMR (400 MHz, DMSO-d6) δ 10.58 (s, 1H), 7.65 (s, 1H), 6.40 (s, 2H), 5.37 (t, J=8.9 Hz, 1H), 5.14 (s, 1H), 5.08 (d, J=3.2 Hz, 1H), 4.61 (s, 1H), 4.18 (m, 3H), 2.73 (s, 1H), 2.34-2.26 (in, 3H), 2.10-2.04 (m, 1H)), 1.54-1.51 (m, 2H), 1.22 (s, 52H), 0.85 (t, J=6.7 Hz, 3H).

Example 15 Preparation of Entecavir-5'-chenodeoxycholate

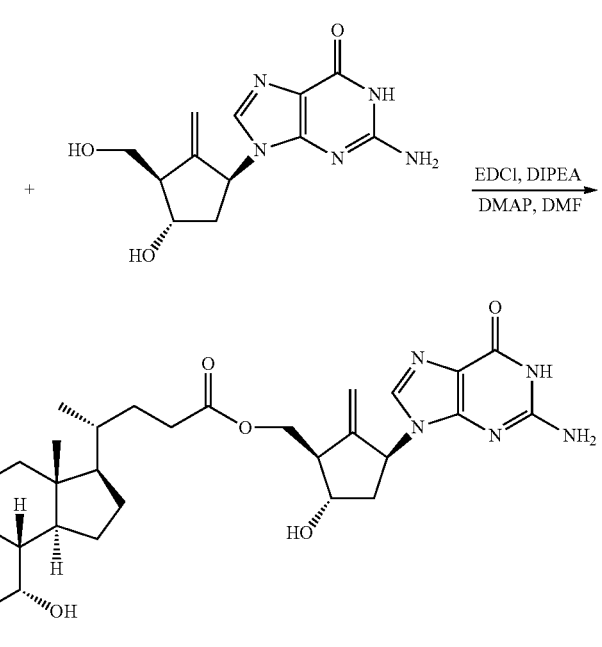

The process step was performed with reference to the method of Example 5, except that the ursodesoxycholic acid was replaced with chenodeoxycholic acid. After the reaction product was separated and purified, the compound 18 of Entecavir-5'-chenodeoxycholate was obtained, with a yield of 20.09%.

$^1$H NMR (500 MHz, DMSO-d6) δ 10.59 (s, 1H), 7.66 (s, 1H), 6.41 (s, 2H), 5.37 (t, J=9.1 Hz, 1H), 5.15 (s, 1H), 5.07 (d, J=3.2 Hz, 1H), 4.61 (s, 1H), 4.43 (d, J=4.6 Hz, 1H), 4.17 (m, 3H), 3.86 (d, J=6.8 Hz, 1H), 3.31-3.23 (m, 2H), 2.73 (s, 1H), 2.42-2.20 (m, 3H), 2.12-2.03 (m, 1H), 1.92 (d, J=11.6 Hz, 1H), 1.88-1.77 (m, 1H), 1.77-1.59 (m, 4H), 1.47-1.34 (m, 18H), 0.89 (d, J=6.5 Hz, 4H), 0.86 (s, 3H), 0.60 (s, 3H).

Example 16 Preparation of
Entecavir-5'-hyodeoxycholate

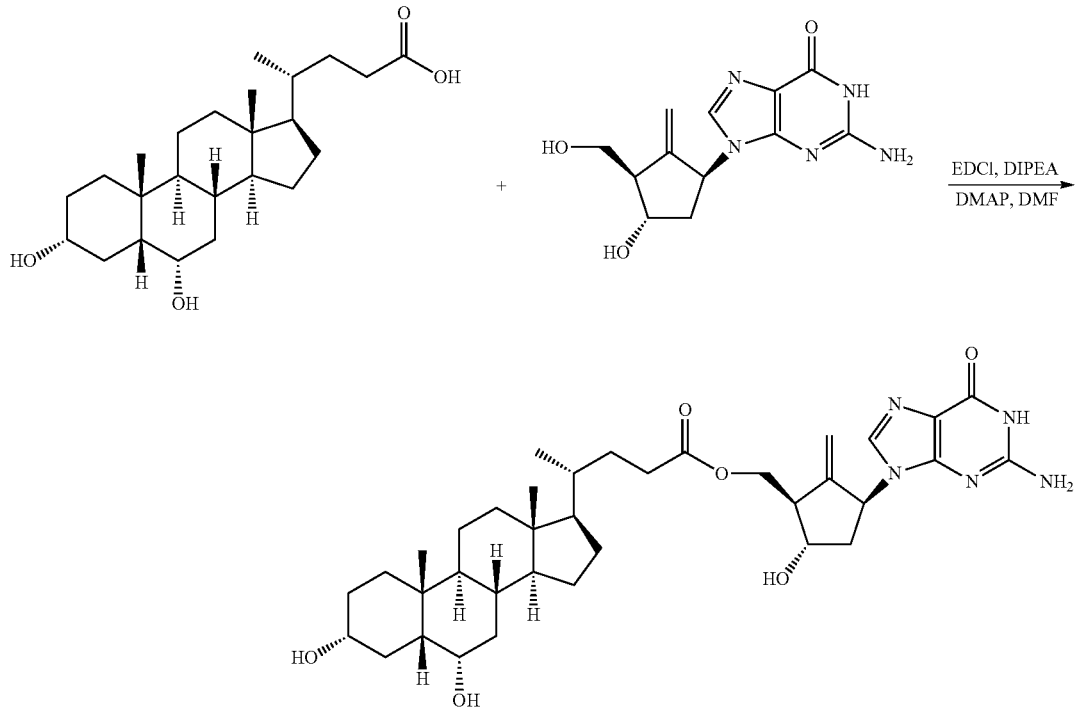

The process step was performed with reference to the method of Example 5, except that the ursodesoxycholic acid was replaced with hyodeoxycholic acid. After the reaction product was separated and purified, the compound 19 of Entecavir-5'-hyodeoxycholate was obtained, with a yield of 23.50%.

$^1$H NMR (500 MHz, DMSO-d6) δ 10.59 (s, 1H), 7.66 (s, 1H), 6.41 (s, 2H), 5.37 (t, J=9.1 Hz, 1H), 5.15 (s, 1H), 5.07 (d, J=3.2 Hz, 1H), 4.61 (s, 1H), 4.23 (d, J=4.6 Hz, 1H), 4.17 (m, 3H), 3.66 (d, J=6.8 Hz, 1H), 3.31-3.23 (m, 2H), 2.73 (s, 1H), 2.12-2.20 (m, 3H), 2.12-2.03 (m, 1H), 1.92 (d, J=11.6 Hz, 1H), 1.88-1.77 (m, 1H), 1.77-1.59 (in, 4H), 1.47-1.34 (m, 18H), 0.89 (d, J=6.5 Hz, 4H), 0.86 (s, 3H), 0.60 (s, 3H).

Example 17 Preparation of
Entecavir-5'-deoxycholate

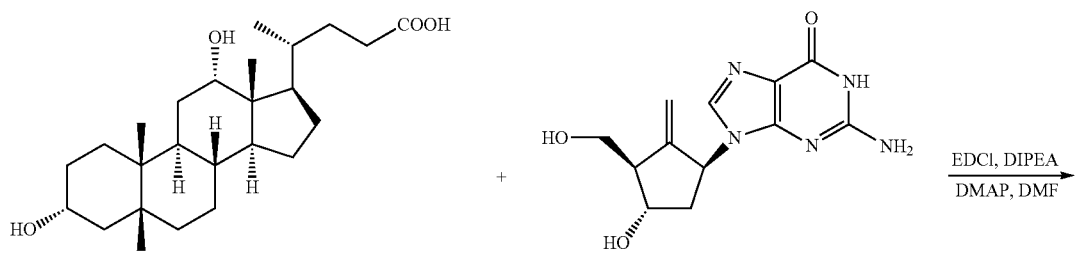

-continued

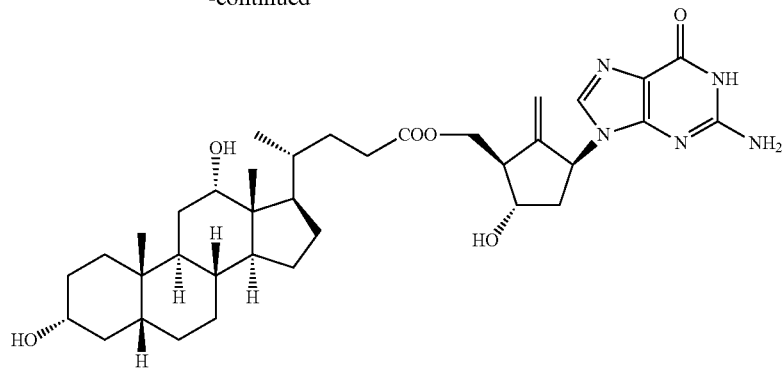

20

The process step was performed with reference to the method of Example 5, except that the ursodesoxycholic acid was replaced with deoxycholic acid. After the reaction product was separated and purified, the compound 20 of Entecavir-5'-deoxycholate was obtained, with a yield of 17.95%.

$^1$H NMR (500 MHz, DMSO-d6) δ 10.59 (s, 1H), 7.66 (s, 1H), 6.41 (s, 2H), 5.37 (t, J=9.1 Hz, 1H), 5.15 (s, 1H), 5.07 (d, J=3.2 Hz, 1H), 4.61 (s, 1H), 4.37 (d, J=4.6 Hz, 1H), 4.17 (m, 3H), 3.80 (d, J=6.8 Hz, 1H), 3.31-3.23 (m, 2H), 2.73 (s, 1H), 2.42-2.20 (in, 3H), 2.12-2.03 (m, 1H), 1.92 (d, J=11.6 Hz, 1H), 1.88-1.77 (m, 1H), 1.77-1.59 (m, 4H), 1.57-1.34 (m, 18H), 0.89 (d, J=6.5 Hz, 4H), 0.86 (s, 3H), 0.68 (s, 3H).

Example 18 Preparation of Entecavir-5'-lauroylamidobutanoate

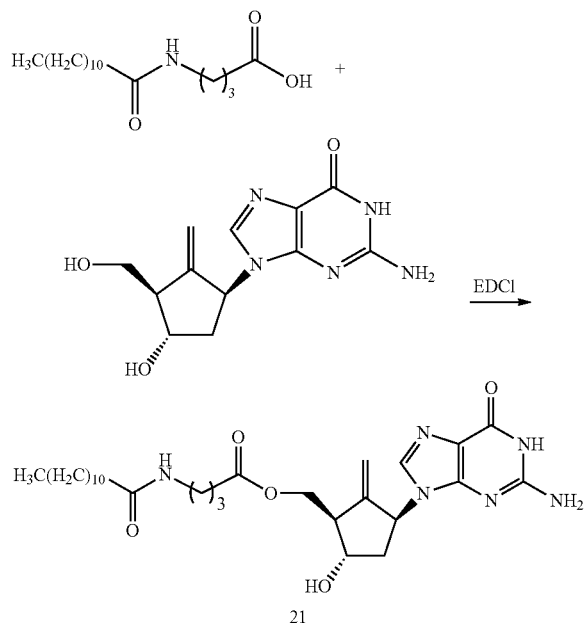

21

The process step was performed with reference to the method of Example 8 by taking lauroylamidobutanoic acid as the material, and the compound 21 of Entecavir-5'-lauroylamidobutanoate was obtained, with a yield of 27.38%.

$^1$H NMR (500 MHz, DMSO-d6) δ10.56 (s, 1H), 7.75 (t, J=5.5 Hz, 1H), 7.65 (s, 1H), 6.37 (s, 2H), 5.38 (t, J=9.0 Hz, 1H), 5.14 (s, 1H), 5.07 (d, J=3.0 Hz, 1H), 4.60 (s, 1H), 4.18 (m, 3H), 3.06 (m, 2H), 2.75 (br, 1H), 2.34 (t, 0.1=7.5 Hz, 2H), 2.30 (m, 1H), 2.07 (m, 1H), 2.03 (t, J=7.5 Hz, 2H), 1.66 (m, 2H), 1.46 (m, 2H), 1.23 (s, 16H), 0.85 (t, J=7.0 Hz, 3H).

Example 19 Preparation of Entecavir-5'-stearoylamidobutanoate

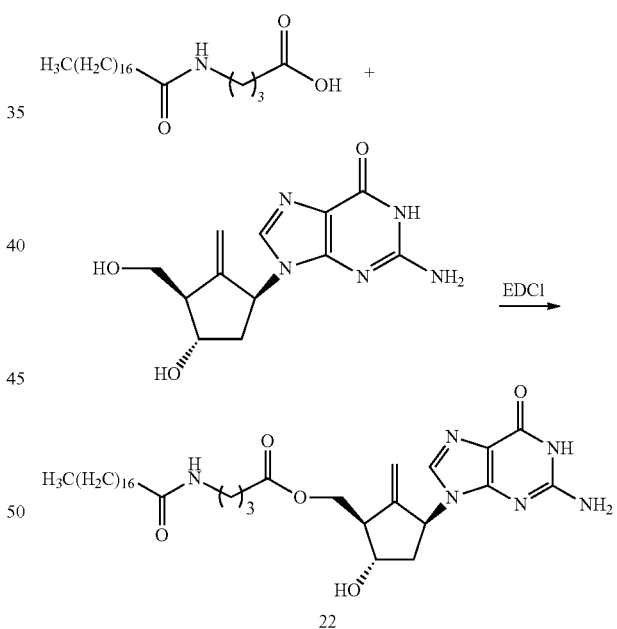

22

The process step was performed with reference to the method of Example 8 by taking stearoylamidobutanoic acid as the material, and the compound 22 of Entecavir-5'-stearoylamidobutanoate was obtained, with a yield of 32.01%.

$^1$H NMR (500 MHz, DMSO-d6) δ 10.55 (s, 1H), 7.77 (t, J=5.5 Hz, 1H), 7.66 (s, 1H), 6.37 (s, 2H), 5.38 (t, J=9.0 Hz, 1H), 5.15 (s, 1H), 5.07 (d, J=3.0 Hz, 1H), 4.61 (s, 1H), 4.18 (m, 3H), 3.06 (m, 2H), 2.74 (br, 1H), 2.34 (t, J=7.5 Hz, 2H), 2.30 (m, 1H), 2.07 (m, 1H), 2.03 (t, J=7.5 Hz, 2H), 1.66 (m, 2H), 1.46 (m, 2H), 1.23 (s, 28H), 0.85 (t, J=7.0 Hz, 3H).

Example 20 Preparation of Entecavir-5'-icosanamidobutanoate

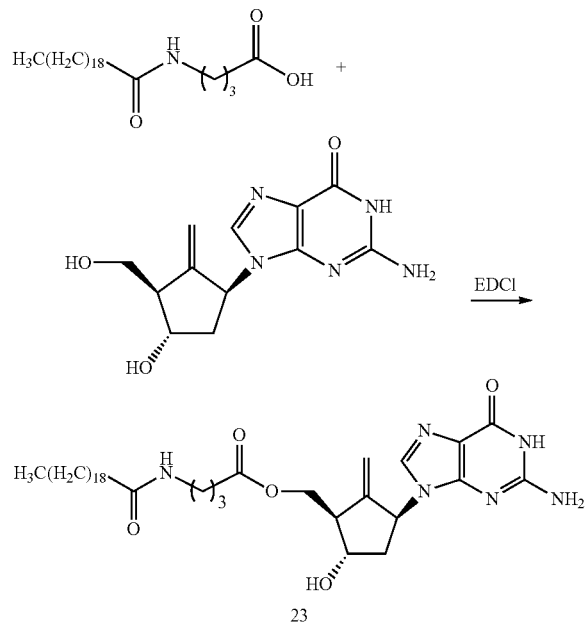

The process step was performed with reference to the method of Example 8 by taking icosanamidobutanoic acid as the material, and the compound 23 of Entecavir-5'-icosanamidobutanoate was obtained, with a yield of 35.96%.

$^1$H NMR (500 MHz, DMSO-d6) δ 10.55 (s, 1H), 7.76 (t, J=5.5 Hz, 1H), 7.67 (s, 1H), 6.37 (s, 2H), 5.36 (t, J=9.0 Hz, 1H), 5.15 (s, 1H), 5.07 (d, J=3.0 Hz, 1H), 4.62 (s, 1H), 4.18 (m, 3H), 3.04 (m, 2H), 2.74 (br, 1H), 2.35 (t, J=7.5 Hz, 2H), 2.30 (m, 1H), 2.05 (m, 1H), 2.02 (t, J=7.5 Hz, 2H), 1.66 (m, 2H), 1.46 (m, 2H), 1.23 (s, 32H), 0.85 (t, J=7.0 Hz, 3H).

Example 21 Pharmacokinetic Test of Entecavir-5'-docosanoate, Entecavir-5'-ursodesoxycholate and Entecavir-5'-stearoylamidobutanoate in the Body of Beagle Three conventional male beagles were used in the test, and they were forbidden to eat for 12 hours before administering drugs, and drank water freely meanwhile. Entecavir-5'-docosanoate (prepared in Example 4), Entecavir-5'-ursodesoxycholate (prepared in Example 5) and entecavir-5'-stearoylamidobutanoate (prepared in Example 19) were used to prepare a suspension, and were intramuscularly injected in a dosage of 0.508 mg/kg, 0.552 mg/kg, and 0.533 mg/kg respectively. Before drug administration and 1 hour, 2 hours, 4 hours, 8 hours, 12 hours, 18 hours, 24 hours, 48 hours, 96 hours, 144 hours, 192 hours, 240 hours, 288 hours, and 360 hours after drug administration, 1.0 mL whole blood of the beagle was collected from venous vein in front legs each time and centrifuged in an heparinized centrifuge tube at 6000 rpm for 10 minutes, to separate blood plasma, and the blood plasma was preserved at −80° C. to be measured.

Figure 2:
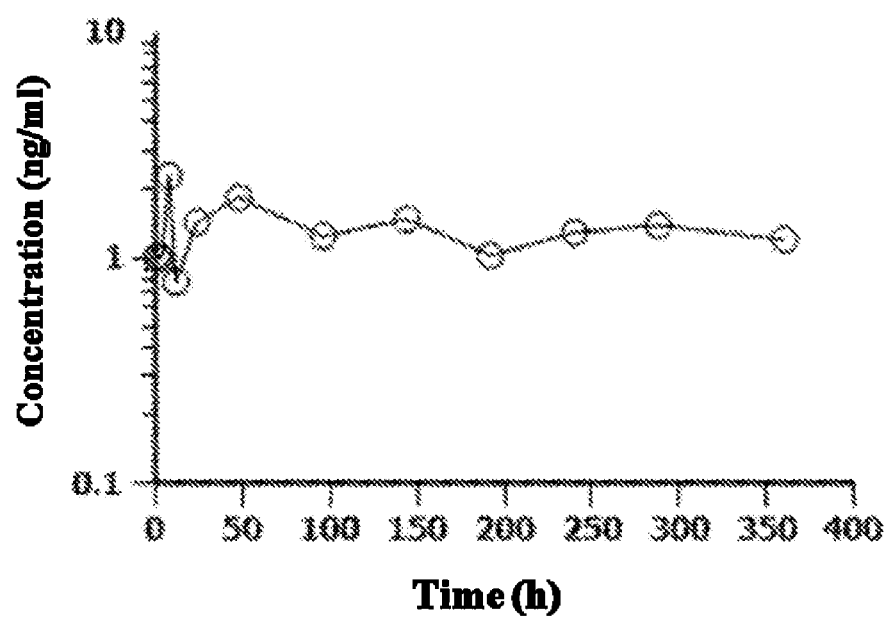
FIG. 2 shows a change of blood concentration of Entecavir after Entecavir-5'-ursodesoxycholate was administered to a beagle.
Figure 3:
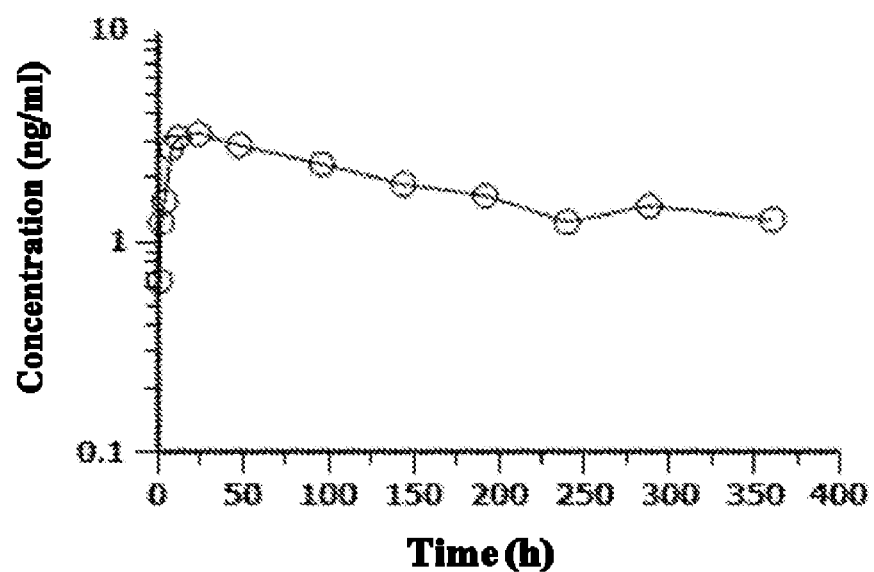
FIG. 3 shows a change of blood concentration of Entecavir after Entecavir-5'-stearoylamidobutanoate was administered to a beagle.

Treatment of blood plasma sample: 100 μL of blood plasma sample was added to 20 μL of methanol-water (V:V, 1:1) and 20 μL of interior label (2 μg/mL apigenin), and mixed through vortex. 200 μL of methanol was added and mixed through vortex, followed by being centrifuged under a centrifugal force of 14,000 g for 30 minutes. 10 μL of supernate was collected for analysis. The results are shown in Table 1, Table 2, and Table 3, as well as FIG. 1, FIG. 2 and FIG. 3.

TABLE 1

BLOOD DRUG CONCENTRATION OF ENTECAVIR AFTER ENTECAVIR-5'-BEHENATE (0.508 mg/kg) WAS INTRAMUSCULARLY INJECTED INTO THE BEAGLE

| t(h) | CONCENTRATION ng/ml |
|---|---|
| 0.5 | ND |
| 1 | 0.18 |
| 2 | 0.3 |
| 4 | 2.07 |
| 8 | 6.6 |
| 12 | 15.6 |
| 18 | 639 |
| 24 | 3.19 |
| 48 (2 days) | 0.52 |
| 96 (4 days) | 1.08 |
| 144 (6 days) | 0.76 |
| 192 (8 days) | 1.03 |
| 240 (10 days) | 1.26 |

TABLE 2

BLOOD DRUG CONCENTRATION OF ENTECAVIR AFTER ENTECAVIR-5'-URSODESOXYCHOLATE (0.552 mg/kg) WAS INTRAMUSCULARLY INJECTED INTO THE BEAGLE

| TIME | CONCENTRATION ng/ml |
|---|---|
| 1 | 0.997 |
| 2 | 1.04 |
| 4 | 1.00 |
| 8 | 2.31 |
| 12 | 0.785 |
| 24 | 1.44 |
| 48 (2 days) | 1.86 |
| 96 (4 days) | 1.25 |
| 144 (6 days) | 1.49 |
| 192 (8 days) | 1.03 |
| 240 (10 days) | 1.3 |
| 288 (12 days) | 1.4 |
| 360 (15 days) | 1.21 |

TABLE 3

BLOOD DRUG CONCENTRATION OF ENTECAVIR AFTER ENTECAVIR-5'-STEAROYLAMINOBUTYRATE (0.533 mg/kg) WAS INTRAMUSCULARLY INJECTED INTO THE BEAGLE

| TIME | CONCENTRATION ng/ml |
|---|---|
| 1 | 0.653 |
| 2 | 1.24 |
| 4 | 1.55 |
| 8 | 2.78 |
| 12 | 3.12 |
| 24 | 3.25 |
| 48 (2 days) | 2.86 |
| 96 (four days) | 2.33 |
| 144 (6 days) | 1.87 |
| 192 (8 days) | 1.65 |
| 240 (10 days) | 1.24 |
| 288 (12 days) | 1.48 |
| 360 (15 days) | 1.27 |

Test results: the compound of the present disclosure can be effective in a long term in the body of animals. Particularly, injectable suspensions of Entecavir-5'-docosanoate, Entecavir-5'-ursodesoxycholate and entecavir-5'-stearoylamidobutanoate can be released sustainably and steady after being intramuscularly injected to the beagle, thus to achieve a long-acting effect.

The compound of the present disclosure is suitable for preparing long-acting suspensions. It can be effective in a long term in the body due to proper solubility and dissolving speed, and is safe and reliable.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

What is claimed is:

1. A compound of formula I, or a stereoisomer, or a pharmaceutically acceptable salt thereof,

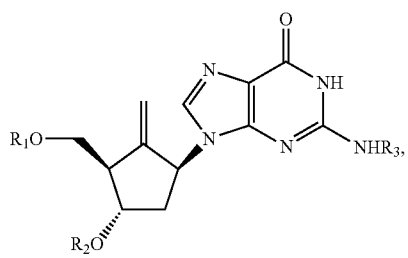

I wherein, $R_1$ is —C(=O)—$X_1$—$Y_1$, and both $R_2$, and $R_3$ are H, and wherein either:
   a) $X_1$ is selected from O, NH, $(CH_2)_m$, or a chemical bond, and
   $Y_1$ is substituted or unsubstituted —NHC(=O)—$C_{7-30}$ hydrocarbyl, substituted or unsubstituted —C(=O)NH—$C_{7-30}$ hydrocarbyl,
   wherein each substituted hydrocarbyl is optionally substituted with one or more groups independently selected from oxo (=O), thio (=S), halo, amino, —NHC(=O)R, —C(=O)NHR, —C(=O)R, ester group, cycloalkyl, aryl, or heteroaryl; and
   wherein m is an integer from 1 to 6, and R is branched or linear, saturated or unsaturated $C_{1-26}$ hydrocarbyl, or
   b) $X_1$ is a chemical bond, and
   $Y_1$ is branched or linear and saturated or unsaturated $C_{19-29}$ hydrocarbyl, or $Y_1$ is selected from one of the following cholane aliphatic groups:

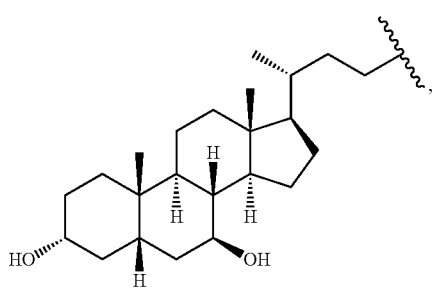

-continued

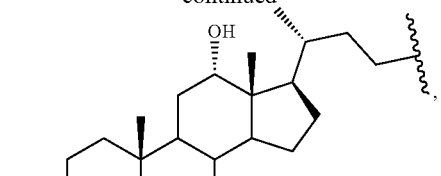

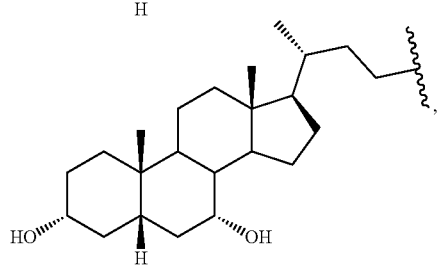

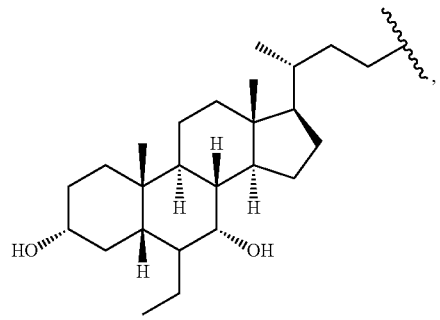

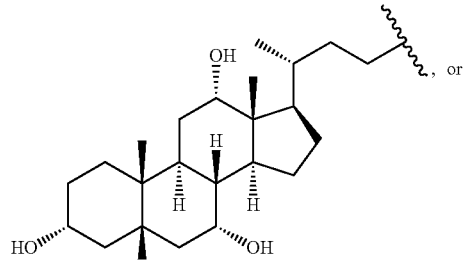

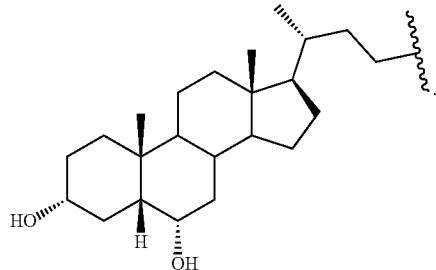

2. The compound of claim 1, or a stereoisomer or a pharmaceutically acceptable salt thereof, wherein $R_1$ is —C(=O)—$X_1$—$Y_1$; $X_1$ is selected from O, $(CH_2)_m$, or a chemical bond; $Y_1$ is substituted or unsubstituted —NHC(=O)—$C_{9-29}$ hydrocarbyl, substituted or unsubstituted —C(=O)NH—$C_{9-29}$ hydrocarbyl, and both $R_2$ and $R_3$ are H;

wherein each substituted hydrocarbyl is optionally substituted with one or more groups independently selected from oxo (=O), thio (=S), F, Cl, amino, —NHC(=O)R, —C(=O)NHR, —C(=O)R, ester group, cycloalkyl, aryl, or heteroaryl; and wherein m is an integer from 1 to 6, and R is branched or linear, saturated or unsaturated $C_{1-26}$ hydrocarbyl; or $R_1$ is —C(=O)—$X_1$—$Y_1$; $X_1$ is selected from O, $(CH_2)_m$, or a chemical bond; $Y_1$ is substituted or unsubstituted —NHC(=O)—$C_{9-27}$ hydrocarbyl, or substituted or unsubstituted —C(=O)NH—$C_{9-27}$ hydrocarbyl, and both $R_2$, and $R_3$ are H;

wherein each substituted hydrocarbyl is optionally substituted with one or more groups independently selected from oxo (=O), thio (=S), F, Cl, amino, —NHC(=O)R, —C(=O)NHR, —C(=O)R, ester group, cycloalkyl, aryl, or heteroaryl; and wherein m is an integer from 1 to 6, and R is branched or linear, saturated or unsaturated $C_{1-26}$ hydrocarbyl.

3. The compound of claim 1, or a stereoisomer or a pharmaceutically acceptable salt thereof, wherein $R_1$ is —C(=O)—$X_1$—$Y_1$, $X_1$ is O or a chemical bond, $Y_1$ is branched or linear, saturated or unsaturated $C_{19-25}$ hydrocarbyl, and both $R_2$ and $R_3$ are H.

4. The compound of claim 1, or a stereoisomer or a pharmaceutically acceptable salt thereof, wherein $R_1$ is $CH_3$—$(CH_2)_n$—C(=O)NH—$(CH_2)_m$—C(=O)—, n is an integer from 6 to 22, m is an integer from 1 to 6, and both $R_2$ and $R_3$ are H; or $R_1$ is $CH_3$—$(CH_2)_n$—C(=O)NH—$(CH_2)_m$—C(=O)—, wherein n is an integer from 10 to 20, m is an integer from 1 to 3, and both $R_2$ and $R_3$ are H.

5. The compound of claim 1, or a stereoisomer or a pharmaceutically acceptable salt thereof, wherein the compound of formula I is selected from one of the following compounds:

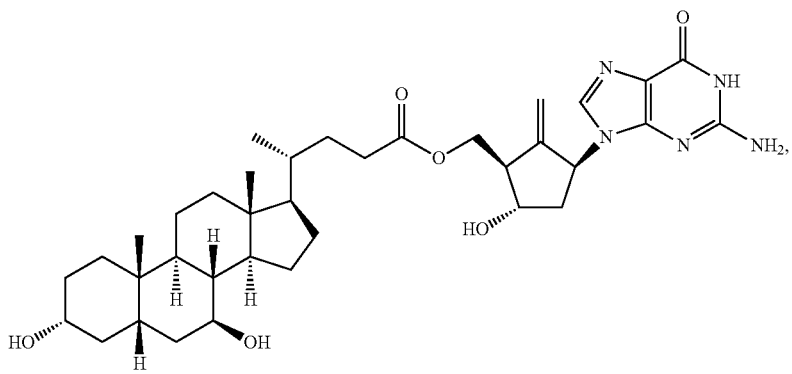

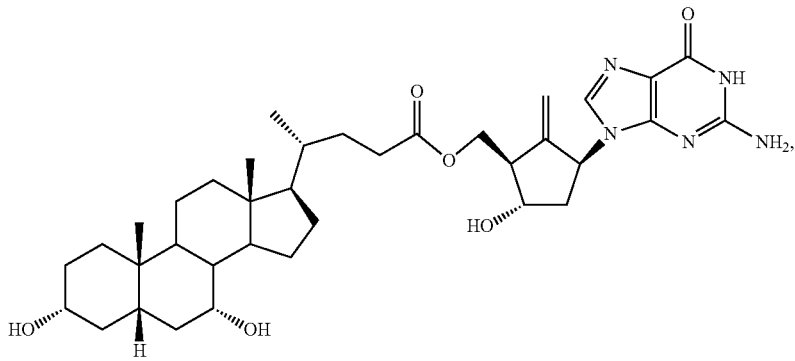

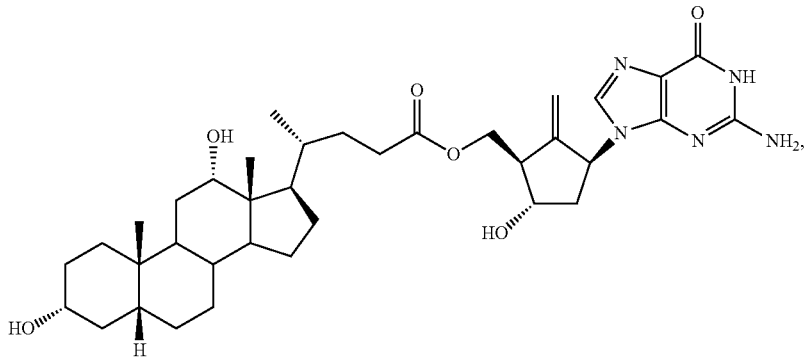

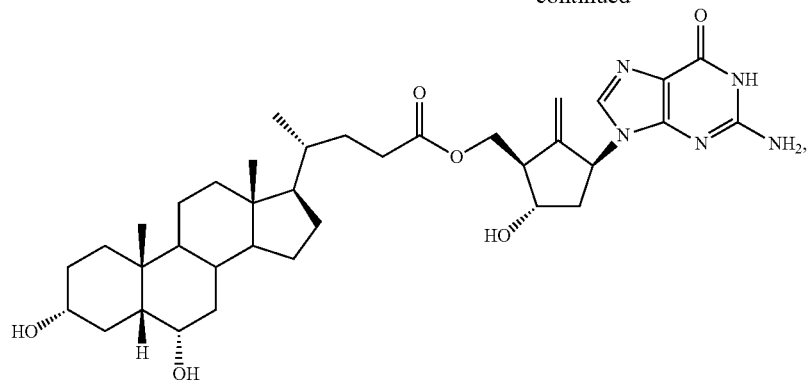
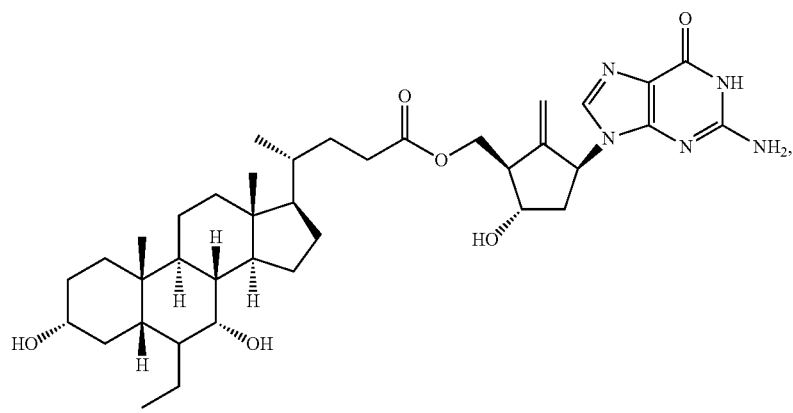
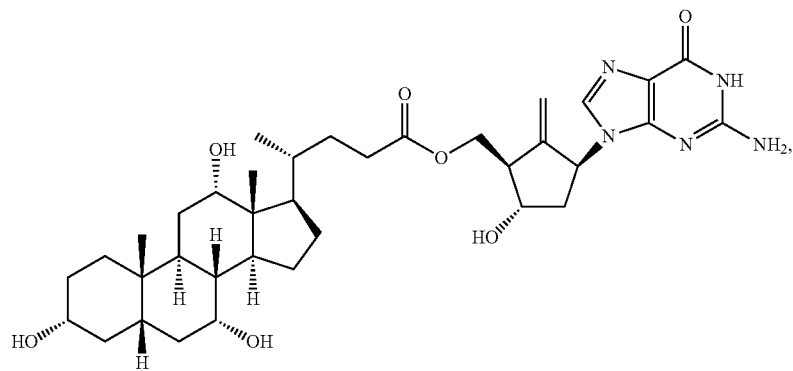
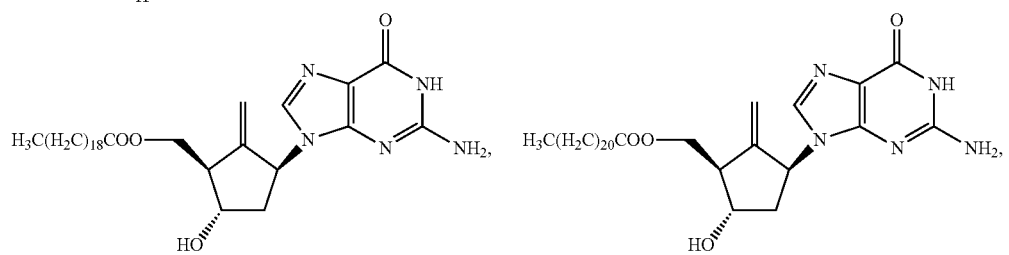
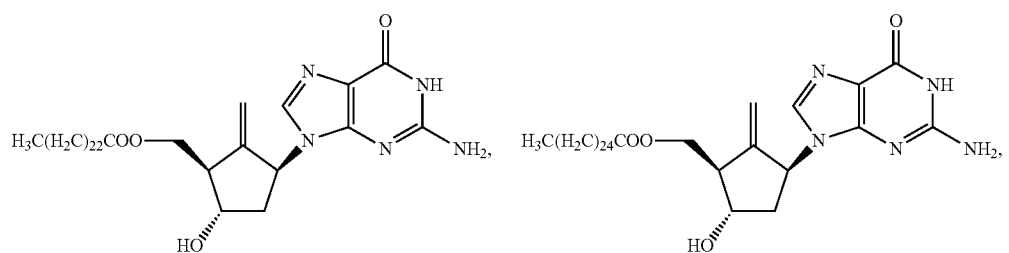

43 44
-continued
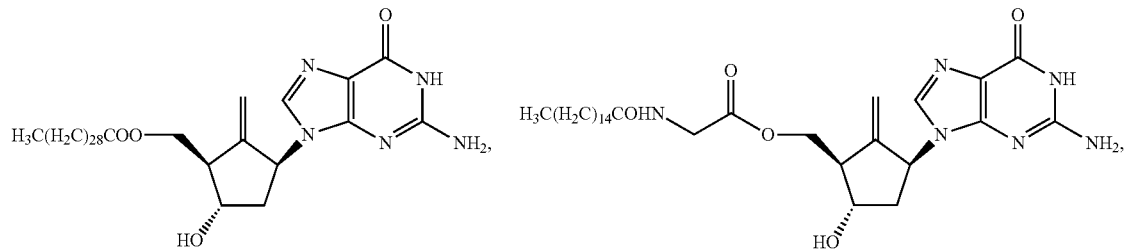
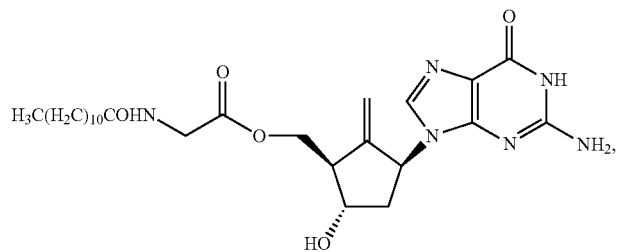
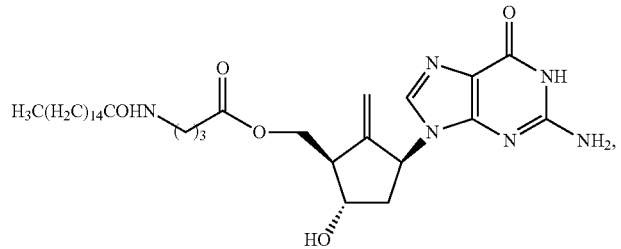
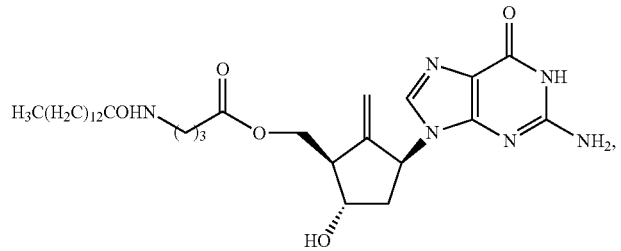
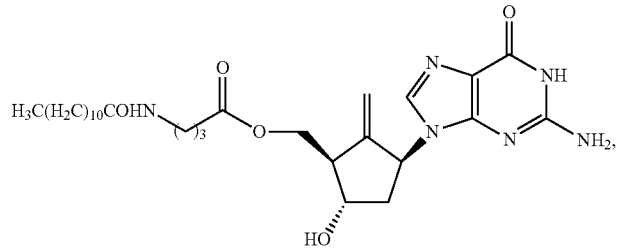
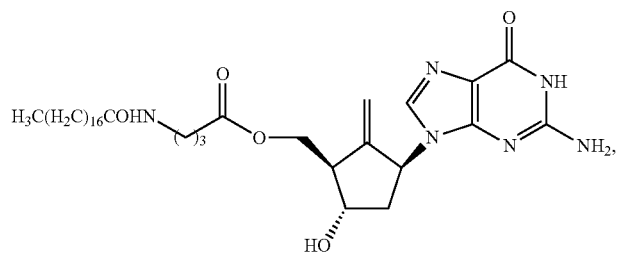

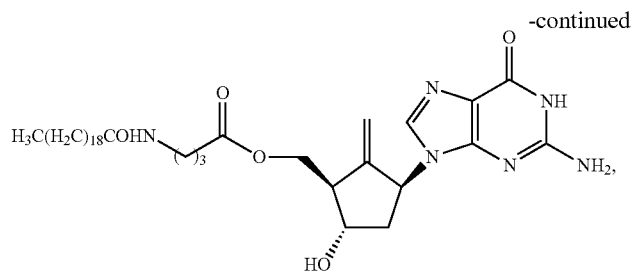

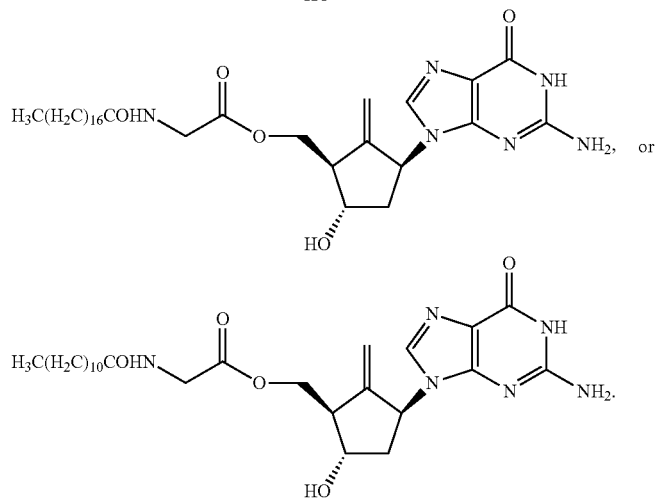

6. A pharmaceutical composition comprising the compound of claim 1, or a stereoisomer or a pharmaceutically acceptable salt thereof, and a pharmaceutically acceptable carrier or excipient, wherein the pharmaceutical composition is in a form of solution for injection, suspension for injection, or sterile powder for injection.

7. A method of preventing and/or treating hepatitis B disease in a subject in need thereof, comprising administering an effective amount of the compound of claim 1, or a stereoisomer or a pharmaceutically acceptable salt thereof, or the pharmaceutical composition to the patients in need thereof.

* * * * *